(12) United States Patent
Phillips

(10) Patent No.: US 7,563,459 B2
(45) Date of Patent: Jul. 21, 2009

(54) METHODS AND COMPOSITIONS FOR REGENERATING TISSUE

(75) Inventor: Catherine A. Phillips, Amarillo, TX (US)

(73) Assignee: The United States of America as represented by the Department of Vetrans Affairs, Washington, DC (US)

( * ) Notice: Subject to any disclaimer, the term of this patent is extended or adjusted under 35 U.S.C. 154(b) by 0 days.

(21) Appl. No.: 11/788,643

(22) Filed: Apr. 20, 2007
(Under 37 CFR 1.47)

(65) Prior Publication Data

US 2007/0243175 A1  Oct. 18, 2007

Related U.S. Application Data

(63) Continuation of application No. 10/388,964, filed on Mar. 14, 2003, now Pat. No. 7,282,222.

(60) Provisional application No. 60/364,498, filed on Mar. 15, 2002.

(51) Int. Cl.
*A61K 35/28* (2006.01)
*A61K 35/26* (2006.01)
*A01N 25/00* (2006.01)

(52) U.S. Cl. .................... 424/577; 514/885

(58) Field of Classification Search ................ None
See application file for complete search history.

(56) References Cited

U.S. PATENT DOCUMENTS

| | | |
|---|---|---|
| 4,466,951 A | 8/1984 | Pittman |
| 4,735,210 A | 4/1988 | Goldenberg |
| 4,797,368 A | 1/1989 | Carter et al. |
| 4,801,533 A | 1/1989 | Fudenberg |
| 4,859,449 A | 8/1989 | Mattes |
| 4,959,216 A | 9/1990 | Daunter |
| 4,970,154 A | 11/1990 | Chang |
| 5,032,678 A | 7/1991 | Washino et al. |
| 5,043,260 A | 8/1991 | Jauregui |
| 5,057,301 A | 10/1991 | Wilbur et al. |
| 5,089,604 A | 2/1992 | Washino et al. |
| 5,098,843 A | 3/1992 | Calvin |
| 5,118,798 A | 6/1992 | Washino et al. |
| 5,128,257 A | 7/1992 | Baer |
| 5,166,320 A | 11/1992 | Wu et al. |
| 5,173,414 A | 12/1992 | Lebkowski et al. |
| 5,254,342 A | 10/1993 | Shen et al. |
| 5,262,176 A | 11/1993 | Palmacci et al. |
| 5,270,199 A | 12/1993 | Ezekowitz |
| 5,279,833 A | 1/1994 | Rose |
| 5,284,646 A | 2/1994 | Menz et al. |
| 5,322,682 A | 6/1994 | Bartzokis et al. |
| 5,331,094 A | 7/1994 | Eppler et al. |
| 5,342,607 A | 8/1994 | Josephson |
| 5,346,696 A | 9/1994 | Kim et al. |
| 5,352,432 A | 10/1994 | Menz et al. |
| 5,352,670 A | 10/1994 | Venot et al. |
| 5,399,346 A | 3/1995 | Anderson et al. |
| 5,460,831 A | 10/1995 | Kossovsky et al. |
| 5,486,359 A | 1/1996 | Caplan et al. |
| 5,490,991 A | 2/1996 | Enriquez et al. |
| 5,512,294 A | 4/1996 | Li et al. |
| 5,525,503 A | 6/1996 | Rudd et al. |
| 5,527,884 A | 6/1996 | Russell et al. |
| 5,545,130 A | 8/1996 | Hofmann et al. |
| 5,547,932 A | 8/1996 | Curiel et al. |
| 5,554,386 A | 9/1996 | Groman et al. |
| 5,608,060 A | 3/1997 | Axworthy et al. |
| 5,616,690 A | 4/1997 | Axworthy et al. |
| 5,624,896 A | 4/1997 | Axworthy et al. |
| 5,635,383 A | 6/1997 | Wu et al. |
| 5,656,609 A | 8/1997 | Wu et al. |
| 5,679,323 A | 10/1997 | Menz et al. |
| 5,683,866 A | 11/1997 | Sarkar et al. |
| 5,693,763 A | 12/1997 | Codington et al. |

(Continued)

FOREIGN PATENT DOCUMENTS

WO   WO 91/06309   5/1991

(Continued)

OTHER PUBLICATIONS

Abrahamsen et al, "Stimulatory effect of counterflow centrifugal elutriation in large-scale separation of peripheral blood monocytes can be reversed by storing the cells at 37° c," *J. Clin. Apheresis* 6(1):48-53 (1991).

(Continued)

*Primary Examiner*—Michail A Belyavskyi
(74) *Attorney, Agent, or Firm*—BioTechnology Law Group; Daniel M. Chambers

(57) ABSTRACT

The present invention is directed to methods for delivering cells to a target tissue in a mammal using glycoconjugate to traffic the cell to a desired organ in the mammal. The methods according to the present invention are especially applicable to administering stem cells such as those derived from the bone marrow or from umbilical cord tissue. The methods are also useful for targeting a gene of interest to a tissue in a mammal by introducing a cell containing the gene of interest and administering a glycoconjugate to the mammal.

6 Claims, 4 Drawing Sheets

U.S. PATENT DOCUMENTS

| | | | |
|---|---|---|---|
| 5,697,902 | A | 12/1997 | Goldenberg |
| 5,719,020 | A | 2/1998 | Liav et al. |
| 5,728,399 | A | 3/1998 | Wu et al. |
| 5,728,518 | A | 3/1998 | Carmichael |
| 5,837,539 | A | 11/1998 | Caplan et al. |
| 6,146,614 | A | 11/2000 | Rubin et al. |
| 6,406,699 | B1 | 6/2002 | Wood |
| 7,282,222 | B2 | 10/2007 | Phillips |
| 2006/0171883 | A1 | 8/2006 | Phillips et al. |
| 2006/0171934 | A1 | 8/2006 | Phillips |
| 2007/0110734 | A9 | 5/2007 | Phillips |
| 2007/0196331 | A1 | 8/2007 | Phillips et al. |
| 2007/0243173 | A1 | 10/2007 | Phillips |
| 2007/0243174 | A1 | 10/2007 | Phillips et al. |

FOREIGN PATENT DOCUMENTS

| | | |
|---|---|---|
| WO | WO 93/24640 | 12/1993 |
| WO | WO 93/24641 | 12/1993 |
| WO | WO 94/26877 | 11/1994 |
| WO | WO 98/50527 | 11/1998 |
| WO | WO 00/63253 | 10/2000 |
| WO | WO 01/24771 | 4/2001 |
| WO | WO 03/077864 | 9/2003 |
| WO | WO 03/077865 | 9/2003 |
| WO | WO 03/105908 | 12/2003 |

OTHER PUBLICATIONS

Aebersold et al, "A simplified automated procedure for generation of human lymphokine-activated killer cells for use in clinical trials," *J. Immunol. Methods* 112:1-7 (1988).

Anderson et al, "Toxicity of human recombinant interleukin-2 in the mouse is mediated by interleukin-activated lymphocytes," *Lab. Invest.* 59(5):598-612 (1988).

Angelini et al, "Stem Cell Treatment of the Heart," *Tex. Heart Inst. J.* 32(4):479-488 (2005).

Arosarena, "Tissue engineering," Curr. Opin. Otolaryngol. Head Neck Surg. 13(4):233-241 (2005).

Ashwell, "The role of cell-surface carbohydrates in binding phenomena," *Mammalian Cell Membranes*, vol. 4(3):57-71, Butterworth, London (1977).

Ashwell et al, "The role of surface carbohydrates in the hepatic recognition and transport of circulating glycoproteins," *Adv. Enzymol. Relat. Areas Mol. Biol.* 41:99-128 (1974).

Ashwell et al, "Carbohydrate-Specific Receptors of the Liver," *Ann. Rev. Biochem.* 51:531-554 (1982).

Audet, "Stem cell bioengineering for regenerative medicine," Expert Opin. Biol. Ther. 4(5):631-644 (2004).

Balsam et al, "Haematopoietic stem cells and repair of the ischaemic heart," Clinical Science 109(6):483-492 (2005).

Balsam et al, "Haematopoietic stem cells adopt mature haematopoietic fates in ischaemic myocardium," Nature 428(6983):668-673 (2004).

Bennett et al, "Immunosuppression by Human Plasma α1-Acid Glycoprotein: Importance of the Carbohydrate Moiety," Proc. Natl. Acad. Sci. USA 77(10):6109-6113 (1980).

Boheler et al, "Can exogenous stem cells be used in transplantation?," *Cells, Tissues, Organs* 65(3-4):237-245 (1999).

Brenner et al, "Gene transfer into human hematopoietic progenitor cells: A review of current clinical protocols," *J. Hematother.* 2(1):7-17 (1993).

Brossart et al, "Identification of HLA-A2-restricted T-cell epitopes derived from the MUC1 tumor antigen for broadly applicable vaccine therapies," *Blood* 93(12):4309-4317 (1999).

Buchschacher et al, "Human immunodeficiency virus vectors for inducible expression of foreign genes," *J. Virol.* 66(5):2731-2739 (1992).

Budker et al, "pH-sensitive, cationic liposomes: A new synthetic virus-like vector," *Nature Biotechnology* 14(6):760-764 (1996).

Carter et al, "Technical aspects of lymphokine-activated killer cell production," *J. Clin. Apheresis* 4(2-3):113-117 (1988).

Carter et al, "Use of a continuous-flow cell separator in density gradient isolation of lymphocytes," *Transfusion* 27(4):362-365 (1987).

Chang et al, "Adoptive immunotherapy with vaccine-primed lymph node cells secondarily activated with anti-CE3 and interleukin-2," *J. Clin. Oncol.* 15(2):796-807 (1997).

Chang et al, "Current status of adoptive immunotherapy of cancer," *Crit. Rev. Oncol.-Hematol.* 22(3):213-228 (1996).

Chen et al, "A gene therapy approach for treating T cell mediated autoimmune diseases," *Blood* 97(4):886-894 (2001).

Chien, "Lost and found: cardiac stem cell therapy revisited," J. Clin. Invest. 116(7):1838-1840 (2006).

Chin et al, "In vivo distribution of radio-labeled tumor infiltrating lymphocytes in cancer patients," In Vivo 7(1):27-30 (1993).

Cosset et al, "Targeting retrovirus entry," *Gene Therapy* 3(11):946-956 (1996) (Abstract).

Costello et al, "Inhibition of Neutrophil Activation by α1-Acid Glycoprotein," *Clin. Exp. Immunol.* 55(2):465-472 (1984).

Costello et al, "Inhibition of platelet aggregation by native and desialised alpha-1 acid glycoprotein," *Nature* 281:677-678 (1979).

Dillman et al, "Tumor localization by tumor infiltrating lymphocytes labeled with indium-111 in patients with metastatic renal cell carcinoma, melanoma, and colorectal cancer," *Cancer Biother. Radiopharm.* 2(2):65-71 (1997).

Dunn et al, "Low temperature selectivity inhibits fusion between pinocytotic vesicles and lysosomes during heterophagy of $^{125}$I-asialofetuin by the perfused rat liver," *J. Biol. Chem.* 225(12):5971-5978 (1980).

Durant, "Immunotherapy of cancer: The end of the beginning?," *N. Engl. J. Med.* 316(15):939-941 (1987).

Eror et al, "Antiinflammatory effects of soluble complement receptor type 1 promote rapid recovery of ischemia/reperfusion injury in rat small intestine," *Clin. Exp. Immunol.* 90(2):266-275 (1999).

Fagan et al, "Immunotherapy for Cancer: the use of lymphokine-activated killer (LAK) cells," *GUT* 28(2):113-116 (1987).

Felgner et al, "Lipofection: A Highly Efficient, Lipid-Mediated DNA-Transfection Procedure," *Proc. Natl. Acad. Sci. USA* 84(21):7413-7417 (1987).

Gao et al, "The Dynamic in vivo Distribution of Bone Marrow-Derived Mesenchymal Stem Cells after Infusion," *Cells Tissues Organs* 169(1):12-20 (2001).

Gardiner et al, "The therapeutic potential of synthetic multivalent carbohydrates," *Exp. Opin. Invest. Drugs* 7(3):405-411 (1998).

Griffith et al, "In vivo distribution of adoptively transferred indium-111-labeled tumor infiltrating lymphocytes and peripheral blood lymphocytes in patients with metastatic melanoma," *J. Natl. Cancer Inst.* 81(22):1709-1717 (1989).

Hamano et al, "Studies on the kinetics of hemopoietic stem cells and immune responses to the hapten-carrier conjugate," *J. Immunol.* 123(3):1371-1375 (1979).

Harford et al, "The hepatic receptors for asialoglycoproteins," *The Glycoconjugates*, Horowitz ed. 4(B):27-55, Academic Press, NY (1982).

Heath, "Cells for tissue engineering," *TIBECH* 18(1):17-19 (2000).

Hermonat et al, "Use of adeno-associated virus as a mammalian DNA cloning vector: Transduction of neomycin resistance into mammalian tissue culture cells," *Proc. Natl. Acad. Sci. USA* 81(20):6466-6470 (1984).

Hiltbold et al, "Naturally processed class II epitope from the tumor antigen MUC1 primes human CD4+ T cells," *Cancer Res.* 58(22):5066-5070 (1998).

Ho et al, "Stem cells as vehicles for gene therapy: novel strategy for HIV infection," *Stem Cells* 13(Suppl 3):100-105 (1995).

Hogan et al, "Multilineage engraftment in NOD/LtSz-scid/scid mice from mobilized human CD34+ peripheral blood progenitor cells," *Biol. Blood Marrow Transplant.* 3(5):236-246 (1997).

Hsieh et al, "Lysis of primary hepatic tumours by lymphokine activated killer cells," *Gut* 28(2):117-124 (1987).

Inaba et al, "Generation of large numbers of dendritic cells from mouse bone marrow cultures supplemented with granulocyte/macrophage colony-stimulating factor," *J. Exp. Med.* 176(6):1693-1702 (1992).

Johann et al, "GLVR1, a receptor for gibbon ape leukemia virus, is homologous to a phosphate permease of Neurospora crassa and is expressed at high levels in the brain and thymus," *J. Virol.* 66(3):1635-1640 (1992).

Kalos, "Tumor antigen-specific T cells and cancer immunotherapy: current issued and future prospects," *Vaccine* 21(7-8):781-786 (2003).

Keilhoiz et al, "Regional adoptive immunotherapy with interleukin-2 and lymphokine-activated killer (LAK) cells for liver metastasis," *Eur. J. Cancer* 30(1):103-105 (1994).

Kilgore et al, "The Complement System in Myocardial Ischaemia/Reperfusion Injury," *Cardiovasc. Res.* 28(4):437-444 (1994).

Kolb et al, "Interactions between neuraminidase-treated lymphocytes and liver cells," *Function and Structure of the Immune System (Muller-Ruchholtz ed)* 114:219-222 Plenum Press, New York & London (1979).

Kolb-Bachofen et al, "Auto Immune Reactions Against Liver Cells by Syngeneic Neuraminidase Treated Lymphocytes," J. Immunol. 123(6):2830-2834 (1979).

Kotin et al, "Prospects for the Use of Adeno-Associated Virus as a Vector for Human Gene Therapy," *Hum. Gene Ther.* 5(7):793-801 (1994).

Kradin et al, "Tumor-derived interleukin-2-dependent lymphocytes in adoptive immunotherapy of lung cancer," *Cancer Immunol. Immunother.* 24(1):76-85 (1987).

Libert et al, "Protection by alpha 1-acid glycoprotein against tumor necrosis factor- induced lethality," *J. Exp. Med.* 180(4):1571-1575 (1994).

Lotze et al, "The in vivo distributed of autologous human and murine lymphoid cells grow in T Cell growth factor (TCGF)-Implication for the adoptive immunotherapy of tumors," *J. Immunol.* 125(4):1487-1493 (1980).

Mannino et al, "Liposome Mediated Gene Transfer," *BioTechniques* 6(7):682-690 (1988).

Martinez-Maza, "HIV-Induced Immune Dysfunction and AIDS-Associated Neoplasms," *Biological Approaches to Cancer Treatment: Biomodulation*, Mitchell Ed., McGraw-Hill, Inc. 9:181-204 (1993).

Martino et al,"The fate of human peripheral blood lymphocytes after transplantation into SCID mice," *Eur. J. Immunol.* 23(5):1023-1028 (1993).

Miller et al, "Construction and properties of retrovirus packaging cells based on gibbon ape leukemia virus,"*J. Virol.* 65(5):2220-2224 (1991).

Mishra et al, "Stem cell therapy for myocardial regeneration: creating hype ignoring reality," Eur. J. Cardiothoracic Surgery 28(6):909-910 (2005).

Morell et al, "Physical and Chemical Studies on Ceruloplasmin. V. Metabolic Studies on Sialic Acid-Free Ceruloplasmin in Vivo," *J. Biol. Chem.* 243(1):155-159 (1968).

Moritani et al, "Prevention of adoptively transferred diabetes in nonobese diabetic mice with IL-10-transduced islet-specific Th1 lymphocytes: A gene therapy model for autoimmune diabetes," *J. Clin. Invest.* 98(8):1851-1859 (1996).

Muchitsch et al, "In vivo Effect of α1-Acid Glycoprotein on Experimentally Enhanced Capillary Permeability in Guinea-Pig Skin," *Arch. Int. Pharmacodyn.* 331(3):313-321 (1996).

Muchitsch et al, "Effects of Human Alpha-1-Acid Glycoprotein on Aminonucleoside-Induced Minimal Change Nephrosis in Rats," *Nephron.* 81(2):194-199 (1999).

Mueller et al, "Receptor-mediated endocytosis of asialoglycoproteins by rat hepatocytes: receptor-positive and receptor-negative endosomes," *J. Cell. Biol.* 102(3):932-947 (1986).

Mukherji et al, "Imaging pattern of previously in vitro sensitized and interleukin-2 expanded autologous lymphocytes in human cancer," *Int. J. Rad. Appl. Instrum. B*. 15(4):419-427 (1988).

Muul et al, "Development of an Automated Closed System for Generation of Human Lymphokine-Activated Killer (LAK) Cells for use in Adoptive Immunotherapy," *J. Immunol. Methods* 101(2):171-181 (1987).

Muzyczka, "Adeno-associated virus (AAV) vectors: will they work?," *J. Clin. Invst.* 94(4):1351 (1994).

Nelson et al, "Reconstruction and Analysis Methods for Diagnostic ProstaScint Scan Evaluation," *Electromedica* 68:45-48 (2000).

Neubauer et al, "Identification of normal and transformed lymphocyte subsets of nonhuman primates with monoclonal antibodies to human lymphocytes," *J. Immunol* . 130(3):1323-1329 (1983).

Nomura et al, "Targeted gene delivery to the hepatocytes by asialoglycoprotein receptor-mediated endocytosis," *Environ. Medicine* 39(1):17-20 (1995).

Noort et al, "Comparison of repopulating ability of hematopoietic progenitor cells isolated from human umbilical cord blood or bone marrow cells in NOS/SCID mice,"*Bone Marrow Transplantation* (22 Suppl. 1):S58-S60 (1998).

Pereira et al, "Cultured Adherent Cells from Marrow can Serve as Long-Lasting Precursor Cells for Bone, Cartilage, and Lung in Irradiated Mice," *Proc. Natl. Acad. Sci. USA* 92(11):4857-4861 (1995).

Reffelman et al, "Cellular cardiomyoplasty-cardiomyocytes, skeletal myoblasts, or stem cells for regenerating myocardium and treatment of heart failure?," Cardiovasc. Res. 58(2):358-368 (2003).

Rolstad et al, "Natural Killer Cell Activity in the Rat V. The Circulation Patterns and Tissue Localization of Peripheral Blood Large Granular Lymphocytes (LGL)," *J. Immunol.* 136(8):2800-2808 (1986).

Romero et al, "Therapeutic cancer vaccines based on molecularly defined human tumor antigens," *Vaccine* 7(3):405-411 (1998).

Rosenberg et al, "Cancer immunotherapy using interleukin-2 and interleukin-2 activated lymphocytes,"*Ann. Rev. Immunol.* 4:681-709 (1986).

Rosenberg et al, "Immunology of HIV Infection," *Fundamental Immunology Third Edition* (Paul eds) 39:1375-1397Raven Press Ltd., New York (1993).

Rosenberg et al, "A new approach to the adoptive immunotherapy of cancer with tumor-infiltrating lymphocytes," *Science* 233(4770):1318-1321 (1986).

Samlowski et al, "Studies on the liver sequestration of lymphocytes bearing membrane-associated galactose-terminal glycoconjugates: reversal with agents that effectively compete for the asialoglycoprotein receptor," *Cell. Immunol.* 88(2):390-322 (1984).

Samlowski et al, "Bone Marrow Engraftment Efficiency is Enhanced by Competitive Inhibition of the Hepatic Asialoglycoprotein Receptor," *Proc. Natl. Acad. Sci. USA* 82(8):2508-2512 (1985).

Samulski et al, "Helper-free stocks of recombinant adeno-associated viruses: normal integration does not require viral gene expression,"*J. Virol.* 63(9):3822-3828 (1989).

Santin et al, "Development and therapeutic effect of adoptively transferred T cells primed by tumor lysate-pulsed autologous dendritic cells in a patient with metastatic endometrial cancer," *Gynecol. Obstet. Invest*. 49(3):194-203 (2000).

Scheinberg et al, "Hepatic removal of circulating proteins," *Problems in Liver Diseases* Davidson ed., 29:279-285, Stratton Company, NY (1979).

Schnitzer et al, "Quantitation of specific binding of orosomucoid to cultured microvascular endothelium: roel in capillary permeability," *Am. J. Physiol. Heart Circ. Physiol.* 263(1):H48-H55 (1992).

Schwartz et al, "Characterization of the ASGP receptor in a continuous hepatoma line," *J. Biol. Chem.* 256(17):8878-8881 (1981).

Schwartz et al, "Recycling of the ASGP receptor: biochemical and immunocytochemical evidence," *Phil. Trans. R. Soc. Lond.* 300(1099):229-235 (1982).

Simmons et al, "The mobilization of primitive hemopoietic progenitors into peripheral blood," *Stem Cells* 12(Suppl 1):187-201 (1994).

Sommerfelt et al, "Receptor interference groups of 20 retroviruses plating on human cells," *Virol*. 176(1):58-69 (1990).

Spiegel, "The Alpha Interferons: Clinical Overview," *Seminars in Oncol.* 14(2 Suppl 2):1-12 (1987).

Staud et al, "Liver uptake and hepato-biliary transfer of galactosylation," *Biochim. Biophys. Acta* 427(2):183-192 (1999).

Swift et al, "Imaging of metastatic colorectal cancer with tumour-activated killer lymphocytes," *Lancet.* 337(8756):1511-1512 (1991).

Szabolcs et al, "Expansion of immunostimulatory dendritic cells among the myeloid progeny of human CD34+ bone marrow precursors cultured with c-kit ligand, granulocyte-macrophage colony-stimulating factor, and TNF-alpha,"*J. Immunol.* 154(11):5851-5861 (1995).

Taylor-Papadimitriou et al, "MUC1 and cancer," *Biochim. Biophys. Acta* 1455(2-3):301-313 (1999).

Terenishi et al, "Depletion of anti-gal antibodies in baboons by intravenous therapy with bovine serum albumin conjugated to gal oligosaccharides," *Transplantation* 73(1):129-139 (2002).

Tratschin et al, "A human parvovirus, adeno-associated virus, as a eucaryotic vector: transient expression and encapsidation of the procaryotic gene for chloramphenicol acetyltransferase," *Mol. Cell. Biol.* 4(10):2071-2081 (1984).

Tratschin et al, "Adeno-associated virus vector for high-frequency integration, expression, and rescue of genes in mammalian cells," *Mol. Cell. Biol.* 5(11):3251-3260 (1985).

Van Den Hamer et al, "Physical and Chemical Studies on Ceruloplasmin. IX. The Role of Galactosyl Residues in the Clearance of Ceruloplasmin From the Circulation," *J. Biol. Chem.* 245(17):4397-4402 (1970).

Vickers, "More of Less Hematopoietic Stem Cells," *Nature Medicine* 2(12):1281-1282 (1996).

West et al, "Gene expression in adeno-associated virus vectors: The effects of chimeric mRNA structure, helper virus, and adenovirus VA, RNA," *Virol.* 160(1):38-47 (1987).

Wilson et al, "Formation of infectious hybrid virions with gibbon ape leukemia virus and human T-cell leukemia virus retroviral envelope glycoproteins and the gag and pol proteins of Moloney murine leukemia virus," *J. Virol.* 63(5):2374-2378 (1989).

Yu et al, "Intracellular Immunization of Human Fetal Cord Blood Stem/Progenitor Cells with a Ribozyme Against Human Immunodeficiency Virus Type 1," *Proc. Natl. Acad. Sci. USA* 92(3):699-703 (1995).

Aiuti et al., "The Chemokine SDF-1 is a Chemoattractant for Human $CD34^+$ Hematopoietic Progenitor Cells and Provides a New Mechanism to Explain the Mobilization of $CD34^+$ Progenitors to Peripheral Blood," *J. Exp. Med.* 185(1):111-120 (1997).

Aiuti et al., "Human $CD34^+$ cells express CXCR4 and its ligand stromal cell-derived factor-1. Implications for infection by T-cell tropic human immunodeficiency virus," *Blood* 94(1):62-73 (1999).

Aizawa et al., "Marrow uptake to galactosyl-containing neoglycoproteins: Implications in stem cell homing," *Exp. Hematol.* 16(9):811-813 (1988).

Aizawa et al., "Molecular basis of the recognition of intravenously transplanted hematopoietic cells by bone marrow," *Proc. Natl. Acad. Sci. USA* 85(9):3180-3183 (1988).

Alison et al., "Cell differentiation: Hepatocytes from non-hepatic adult stem cells," *Nature* 406(6793):257 (2000).

Anderson et al., "Can Stem cells cross lineage boundaries?," *Nat. Med.* 7(4):393-395 (2001).

Arai et al., "Stromal cells in lymph nodes attract B-lymphoma cells via production of stromal cell-derived factor-1," *Eur. J. Haematol.* 64(5):323-332 (2000).

Barr et al., "Techniques for the chronic cannulation of the jugular vein in mice," *Pharmacol. Biochem. Behav.* 11(1):115-118 (1979).

Bjornson et al., "Turning brain into blood: a hematopoietic fate adopted by adult neural stem cells in vivo," *Science* 283(5401):534-537 (1999).

Bleuel et al., "A Highly Efficacious Lymphocyte Chemoattractant, Stromal Cell-derived Factor 1 (SDF-1)," *J. Exp. Med.* 184(3):1101-1109 (1996).

Bruder et al., "The Effect of Implants Loaded with Autologous Mesenchymal Stem Cells on the Healing of Canine Segmental Bone Defects," *J. Bone Joint Surg. Am.* 80(7):985-996 (1998).

Caplan, "Mesenchymal stem cells," *J. Orthop. Res.* 9(5):641-650 (1991).

Charriaut et al., "Inhibition of in vitro natural killer activity by the third component of complement: Role for C3a fragment," *Proc. Natl. Acad. Sci. USA* 79(19):6003-6007 (1982).

Chen et al., "Therapeutic benefit if intravenous administration of bone marrow stromal cells after cerebral ischemia in rats," *Stroke* 32(4):1005-1011 (2001).

Chopp et al., "Spinal cord injury in rat: Treatment with bone marrow stromal cell transplantation," *NeuroReport* 11(13):3001-3005 (2005).

Collins et al., "Animal Models for Alchol-nicotine interactions," *Alchol and Tobacco: From Basic Science to Clinical Practice*, NIH Publication No. 95-931, Research Monograph No. 30, Washington, D.C., US Government Printing Office, Ch. 7:129-144 (1995).

Cui et al., "Bone marrow cell trafficking following intravenous administration," *Br. J. Haematol.* 107(4-II):895-902 (1999).

Devine et al., "Mesenchymal stem cells are capable of homing to the bone marrow of non-human primates following systemic infusion," *Exp. Hematol.* 29(2):244-255 (2001).

Eglitis et al., "Targeting of marrow-derived astrocytes to the ischemic brain," *NeuroReport* 10(6):1289-1292 (1999).

Ferrari et al., "Muscle regeneration by bone marrow-derived myogenic progenitors," *Science* 279(5356):1528-1530 (1998).

Galli et al., "The kit ligand, stem cell factor," *Adv. Immunol.* 55:1-96 (1994).

Geminder et al., "A Possible Role for CXCR4 and Its Ligand, the CXC Chemokine Stromal Cell-Derived Factor-1, in the Development of Bone Marrow Metastases in Neuroblastoma," *J. Immunol.* 167(8):4747-4757 (2001).

Hall, "Adult stem cells," *Technology Review (MIT)* 104:42-49 (2001).

Hardy et al., "Distribution of homing protein on hemopoietic stromal and progenitor cells," *Exp. Hematol.* 19(9):968-972 (1991).

Hidalgo et al., "Chemokine stromal cell-derived factor-1α modulates $VLA_4$ integrin-dependent adhesion to fibronectin and VCAM-1 on bone marrow hematopoietic progenitor cells," *Exp. Hematol.* 29(3):345-355 (2001).

Horwitz et al., "Transplantability and therapeutic effects of bone marrow-derived mesenchymal cells in children with osteogenesis imperfecta," *Nat. Med.* 5(3):309-313 (1999).

Hou et al., "Osteoblast-specific gene expression after transplantation of marrow cells: Implications for skeletal gene therapy," *Proc. Natl. Acad. Sci. USA* 96(13):7294-7299 (1999).

Jackson et al., "Hematopoietic potential of stem cells isolated from murine skeletal muscle," *Proc. Natl. Acad. Sci. USA* 96(25):14482-14486 (1999).

Jackson et al., "Regeneration of ischemic cardiac muscle and vascular endothelium by adult stem cells," *J. Clin. Invest.* 107(11):1395-1402 (2001).

Kataoka et al., "Identification of lectin-like substances recognizing galactosyl residues of glycoconjugates on the plasma membrane of marrow sinus endothelium," *Blood* 65(5):1163-1171 (1985).

Kawada et al., "Bone marrow origin of hematopoietic progenitors and stem cells in murine muscle," *Blood* 98(7):2008-2013 (2001).

Kim et al., "In Vitro Behavior of Hematopoietic Progenitor Cells Under the Influence of Chemoattractants: Stromal Cell-Derived Factor-1, Steel Factor, and the Bone Marrow Environment," *Blood* 91(1):100-110 (1998).

Kiss et al., "Relationship of $CD34^+$ cell dose to early and late hematopoiesis following autologous peripheral blood stem cell transplantation," *Bone Marrow Transplant.* 19(4):303-310 (1997).

Kocher et al., "Neovascularization if ischemic myocardium by human bone marrow-derived angioblasts prevents cardiomyocyte apoptosis, reduces remodeling and improves cardiac function,"*Nat. Med.* 7(4):430-436 (2001).

Kolb et al., "Lectin Mediates Homing of Sialidase-Treated Erythrocytes of the Liver as Revealed by Scintigraphy," *Hoppe Seylers Z. Physiol. Chem.* 362(12):1609-1614 (1981).

Kolb et al., "Regulation of lymphoid cell traffic," *Immunol. Today* 6(11):318 (1985).

Kolb-Bachofen et al., "Electron Microscopic Evidence for an Asialoglycoprotein Receptor on Kupffer Cells: Localization of Lectin-Mediated Endocytosis," *Cell* 29(3):859-866 (1982).

Kolb-Bachofen et al., "Receptor-mediated Particle Uptake by Liver Macrophages," *Exp. Cell Res.* 148(1):173-182 (1983).

Kolb-Bachofen et al., "GalNAc/Gal-specific rat liver lectins: their role in cellular recognition," *Biol. Cell* 51(2):219-226 (1984).

Kollet et al., "Rapid and efficient homing of human $CD34^+CD38^{-/low}CXCR4^+$ stem and progenitor cells to the bone marrow and spleen of NOD/SCID and NOD/SCID/B2m$^{null}$ mice," *Blood* 97(10):3283-3291 (2001).

Krause et al., "Multi-organ, multi-lineage engraftment by a single bone marrow-derived stem cell," *Cell* 105(3):369-377 (2001).

Lapidot, "Mechanism of Human Stem Cell Migration and Repopulation of NOD/SCID and B2mnull NOS/SCID Mice," *Annu. N.Y. Acad. Sci.* 938:83-95 (2001).

Legasse et al., "Purified hematopoietic stem cells can differentiate into hepatocytes in vivo," *Nat. Med.* 6(11):1229-1234 (2000).

Li et al., "Treatment of stroke in rat with intracarotid administration of marrow stromal cells," *Neurology* 56(12):1666-1672 (2001).

Ma et al., "Impaired B-lymphopoiesis, myelopoiesis, and derailed cerebellar neuron migration in CXCR4 and SDF-1-deficient mice," *Proc. Natl. Acad. Sci. USA* 95(16):9448-9453 (1998).

Mazo et al., "Hematopoietic Progenitor Cell Rolling in Bone Marrow Microvessels: Parallel Contributions by Endothelial Selectins and Vascular Cell Adhesion Molecule 1," *J. Exp. Med.* 188(3):465-474 (1998).

Mohle et al., "The chemokine receptor CXCR-4 is expressed on CD34+ hematopoietic progenitor the leukemic cells and mediates transendothelial migration induced by stromal cell-derived factor-1," *Blood* 91(12):4523-4530 (1998).

Morrison et al., "More or less hematopoietic stem cells: Reply," *Nat. Med.* 2(12):1281-1282 (1996).

Nayier et al., "Stromal derived factor-1-induced chemokinesis of cord blood CD34+ cells (long term culture-initiating cells) through endothelial cells is mediated by E-selectin," *Blood* 94(12):4011-4019 (1999).

Orlic et al., "Bone marrow cells regenerate infracted myocardium," *Nature* 410(6829):701-705 (2001).

Papayannopoulou et al., "The $VLA_4$/VCAM-1 adhesion pathway defines contrasting mechanisms of lodgement of transplanted murine hemotopoietic progenitors between bone marrow and spleen," *Proc. Natl. Acad. Sci. USA* 92(21):9647-9651 (1995).

Pasqualini et al., "Organ targeting In vivo using phage display peptide libraries," *Nature* 380(6572):364-366 (1996).

Peled et al., "The chemokine SDF-1 stimulates integrin-mediated arrest of CD34+ cells on vascular endothelium under shear flow," *J. Clin. Invest.* 104(9):1199-1211 (1999).

Peled et al., "Dependence of human stem cell engraftment and repopulation of NOD/SCID mice on CXCR4," *Science* 283(5403):845-848 (1999).

Pereira et al., "Cultured Adherent Cells from Marrow can Serve as Long-Lasting Precursor Cells for Bone, Cartilage, and Lung in Irradiated Mice," *Proc. Natl. Acad. Sci. USA* 92(11):4857-4861 (1995).

Petersen et al., "Bone Marrow as a Potential Source of Hepatic Oval Cells," *Science* 284(5417):1168-1170 (1999).

Pittenger et al., "Multilineage potential of adult mesenchymal stem cells," *Science* 284(5411):143-147 (1999).

Ponomaryov et al., "Induction of the chemokine stromal-derived factor-1 following DNA damage improves human stem cell function," *J. Clin. Invest.* 106(11):1331-1339 (2000).

Poulsom et al., "Bone marrow contributes to renal parenchymal turnover and regeneration," *J. Pathol.* 195(2):229-235 (2001).

Roos et al., "Galactose-specific receptors on liver cells. II. Characterization of the purified receptor from macrophages reveals no structural relationship to the hepatocyte receptor," *Biochim. Biophys. Acta* 847(1):115-121 (1985).

Samlowski et al., "Characterization of the in vitro interaction of $PNA^{hi}$ lymphocytes with the bone marrow and hepatic asialoglycoprotein receptors," *Cell. Immunol.* 95(1):1-14 (1985).

Schlepper-Schafer et al., "Galactosyl specific receptor on liver cells: binding site for tumor cells," *Eur. J. Cell. Biol.* 25(1):95-102 (1981).

Schlepper-Schafer et al., "Identification of a Receptor for Senescent Erythrocytes on Liver Macrophages," *Biochem. Biophys. Res. Commun.* 115(2):551-559 (1983).

Shen et al., "CXCR-4 Desensitization Is Associated with Tissue Localization of Hemopoietic Progenitor Cells," *J. Immunol.* 166(8):5027-5033 (2001).

Simmons et al., "Vascular cell adhesion molecule-1 expressed by bone marrow stromal cells mediates the binding of hematopoietic progenitor cells," *Blood* 80(2):388-395 (1992).

Springer et al., "Not the usual suspects: the unexpected sources of tissue regeneration," *J. Clin. Invest.* 107(11):1355-1356 (2001).

Stanimirovic et al., "Increase in surface expression of ICAM-1, VCAM-1, and E-selectin in human cerebromicrovascular endothelial cells subjected to ischemia-like insults," *Acta Neurochir. Suppl.* 70:12-16 (1997).

Tavassoli et al., "Molecular basis of homing of intravenously transplanted stem cells to the marrow," *Blood* 76(6):1059-1070 (1990).

Theise et al., "Liver from bone marrow in humans," *Hepatol.* 32(1):11-16 (2000).

Toksoz et al., "Support of human hematopoiesis in long-term bone marrow cultures by murine stromal cells selectively expressing the membrane-bound and secreted forms of the human homolog of the steel gene product, stem cell factor," *Proc. Natl. Acad. Sci. USA* 89(16):7350-7354 (1992).

Tsagurnis et al., "Lack of Evidence for Liver Lectins Functioning as IGM or IGG-FC Receptors," *Biochem. Biophys. Res. Commun.* 130(3):1002-1009 (1985).

Tsuji et al., "Enhancement of murine blast cell colony formation in culture by recombinant rat stem cell factor, ligand for c-kit," *Blood* 78(5):1223-1229 (1991).

Voermans et al., "Adhesion Molecules Involved in Transendothelial Migration of Human Hematopoietic Progenitor Cells," *Stem Cells* 18(6):435-443 (2000).

Wakitani et al., "Mesenchymal cell-based repair of large, full thickness defects of articular cartilage," *J. Bone Joint Surgery* 76(4):579-592 (1994).

Wang et al., "Marrow stromal cells for celluar cardiomyoplasty: Feasibility and potential clinical advantages," *J. Thorac. Cardiovasc. Surg.* 120(5):999-1006 (2000).

William et al., "Increases in oxygen tension stimulate expression of ICAM-1 and VCAM-1 on human endothelial cells," *Am. J. Physiol. Heart Circ. Physiol.* 276(6):2044-2052 (1999).

Wright et al., "Physiological migration of hematopoietic stem and progenitor cells," *Science* 294(5548):1933-1936 (2001).

Young et al., "Use of mesenchymal stem cells in a collagen matrix for Achilles tendon repair," *J. Orthop. Res.* 16(4):406-413 (1998).

METHODS AND COMPOSITIONS FOR REGENERATING TISSUE

RELATED APPLICATIONS

This application claims priority to, the benefit of, and incorporates by reference for all purposes the following commonly owned patent-related documents, each in its entirety: U.S. provisional patent application Ser. No. 60/364498, filed Mar. 15, 2002; and U.S. patent application Ser. No. 10/388,964, filed 14 Mar. 2003, of which this application is a continuation.

GOVERNMENT INTEREST

This invention was funded at least in part by funds supplied by the U.S. government. As a result, the U.S. government may have certain rights in the inventions described herein.

FIELD OF THE INVENTION

The present invention is in the field of clinical medicine and therapy. The invention relates to methods and compositions for targeting cells to an organ of interest.

BACKGROUND OF THE INVENTION

Morell and Ashwell, et al. determined that when a sialyl group of ceruloplasmin is removed by neuraminidase, this plasma protein rapidly disappears from serum. They disclosed that this phenomenon is due to the uptake by the asialoglycoprotein (ASGP) receptor present in liver cells (J. Biol. Chem., vol. 243:155, (1968)). Thereafter, it was reported that the ASGP receptor is present only in liver cells (Adv. Enzymol., vol. 41:99, (1974)). Such specific uptake by liver cells has been identified from the fact that when asialo-ceruloplasmin or asialoorosomucoid, which is experimentally labelled with tritium, is injected into the living body, the isotope is selectively detected only in liver cells (Scheinberg I. H., Morell A. G., Stockert R. J.: Hepatic removal of circulating proteins. Davidson C. S., ed. Problems in Liver Diseases. pp 279-285, New York, Stratton Company, (1979)). In addition, it was also disclosed that this receptor specifically recognizes and absorbs glycoproteins having D-galactose or N-acetylgalactosamine as the terminal sugar group (Ann. Rev. Biochem., vol. 51:531, (1982)). The cell membrane of liver cells comprises a cell structure that combines with asialoglycoprotein terminated with galactose. This cell structure was first named hepato-binding protein (HBP) but is presently called asialoglycoprotein receptor. Further, it has been observed that among various desialylated glycoproteins, the desialylated alpha(1)-acid glycoprotein, asialoorosomucoid, most rapidly disappears from the serum after injection. Therefore, it has been determined that asialo-alpha(1)-acid glycoprotein is both specifically and well taken up by liver cells (J. Biol. Chem., vol. 245:4397 (1970)). The asialoglycoprotein receptor is constituted with a single polypeptide having a molecular weight of about 40,000 and can recognize a glycoprotein having a galactose residue at the nonreductive terminal position of the saccharide chain (i.e., asialoglycoprotein).

While the physiological functions of an asialoglycoprotein receptor are still uncertain, it is believed that an asialoglyroprotein receptor participates in the metabolism of glycoproteins. In fact, the increase of the blood level of an asialoglycoprotein is observed in case of hepatic diseases such as chronic hepatitis, liver cirrhosis and hepatic cancer. Further, the decrease of the quantity of an asialoglycoprotein receptor is observed in an experimental model of hepatic disorder induced by administration of chemicals. In view of these phenomena, it may be possible to diagnose hepatic diseases through assessment of the quantity and quality of an asialoglycoprotein receptor determined by the use of an asialoglycoprotein-like substance, i.e., an asialoglycoprotein receptor-directing compound.

Asialoglycoconjugates have been covalently linked to other agents as a means of targeting chemical (immunosuppressive drugs) and biological agents (antibodies) to be taken up by the liver for therapeutic and diagnostic purposes (see U.S. Pat. Nos. 5,346,696, 5,679,323, and 5,089,604)). In addition, localization of bone marrow stem cells and lymphocytes to the liver has been demonstrated (Samlowski, et al., Cell. Immunol., vol. 88:309-322, (1984); Samlowski, et al., Proc. Natl. Acad. Sci., USA, vol. 82:2508-2512, (1985)).

It is also known that a large proportion of cells infused into mammals adhere to the lung endothelium, independent of cell type or physiological homing properties. It has been observed that stem cells accumulate in the lungs when they are administered (Morrison, et al., Nature Medicine 2:1281-1282 (1996); Martino, et al., Eur. J. Immunol., vol. 23:1023-1028 (1993); Pereira, et al., Proc. Natl. Acad. Sci., USA, vol. 92:4857-4861(1993); and Gao, et al., Cells Tissues Organs, vol. 169:12-20 (2001)).

Orosomucoid, asialo-orosomucoid and agalacto/asialo-orosomucoid have been shown to inhibit neutrophil activation superoxide anion generation, and platelet activation (Costello, et al., Clin. Exp. Immunol., vol. 55:465-472 (1984), and Costello, et al., Nature, vol. 281:677-678 (1979)). These proteins also induced transient immunosuppression and protected against TNF challenge (Bennett, et al., Proc. Natl. Acad. Sci. USA, vol. 77 6109-6113 (1980), and Libert, et al., J. Exp. Med., vol. 180:1571-1575 (1994)). Orosomucoid demonstrated specific binding to pulmonary endothelial cells, which appeared to be independent of carbohydrate recognition sites (Schnitzer, et al., Am. J. Physiol., vol. 263:H48-H55 (1992)). Moreover, orosomucoid was shown to bind to skin capillary endothelial cells in a dose dependent manner, thereby maintaining normal capillary permeability in the face of inflammatory agonists that caused leakage in control animals (Muchitsch, et al., Arch. Int. Pharmacodyn., vol. 331:313-321 (1996)). Similarly, infused orosomucoid bound to kidney capillaries and restored the permselectivity of glomerular filtration (Muchitsch, et al., Nephron, vol. 81:194-199 (1999)).

A stem cell is a special kind of cell that has a unique capacity to renew itself and to give rise to specialized cell types. Although most cells of the body such as heart cells or skin cells are committed to conduct a specific function, a stem cell is uncommitted and remains uncommitted, until it receives a signal to develop into a specialized cell. In 1998, stem cells from early human embryos were first isolated and grown in culture. It is recognized that these stem cells are, indeed, capable of becoming almost all of the specialized cells of the body. In recent years, stem cells present in adults also have been shown to have the potential to generate replacement cells for a broad array of tissues and organs, such as the heart, the liver, the pancreas, and the nervous system. Thus, this class of adult human stem cell holds the promise of being able to repair or replace cells or tissues that are damaged or destroyed by many devastating diseases and disabilities. It is highly useful to effect such therapies by targeting stem cells to particular organs of the body.

In the prior art, adult stem cells generally have been presented to the desired organs either by injection into the tissue or by infusion into the local circulation. A need exists to develop methods for delivery of stem cells through the circulation to specific organs. Such methods would provide a means to target non-invasively solid organs such as the liver, heart, lungs and kidneys. In addition, very diffuse tissues, such as the lung, which are not amenable to dosage by injection could be targeted. Such methods would be useful in regenerative stem cell therapies involving such organs as the liver, heart, lungs and kidneys. The present invention addresses these and other needs.

BRIEF SUMMARY OF THE INVENTION

The present invention features a method for delivering a cell to a target tissue in a mammal comprising the steps of administering a carbohydrate-presenting molecule (e.g., a glycoconjugate) to a mammal and then administering the cell to the mammal. As used here, the term "administering" refers to any method of inducing an increased concentration of the cell in the circulation of the mammal, whether by infusion from an extraneous source or by mobilizing the cell into the circulation from a depot within the mammal, such as the marrow. Means for mobilizing stem cells using for example of GM-CSF and GCSF are well known in the art (see Simmons, et al., The mobilization of primitive hemopoietic progenitors into the peripheral blood. Stem Cells, vol. 12, Suppl. 1:187-201 (1994)). The methods according to the present invention are especially applicable to stem cells, such as those derived from the bone marrow, peripheral blood, umbilical cord or from mesenchymal stem cells expanded in culture. The stem cells within the scope of the invention include any cell capable of differentiating into a desired target tissue. Such cells include pluripotent stem cells, embryonic stem cells, multipotent adult stem cells, and progenitor or precursor cells.

In some embodiments wherein the cell is targeted to the heart, the methods feature administering an orosomucoid (O) or administering an asialoorosomucoid (ASO), and administering the cell to the mammal. In embodiments wherein the cell is targeted to the lungs, the methods feature administering the cell to the mammal in a saline or a serum albumin-saline solution. In embodiments wherein the cell is targeted to the liver, the methods feature administering an orosomucoid or an asialoorosomucoid and administering the cell to the mammal. In embodiments, the orosomucoid is administered concurrently or prior to administering the cell to the mammal. The methods according to the present invention are also useful for either inhibiting or enhancing sequestration of a stem cell in the liver of a mammal even in the absence of targeting the cell to a target organ.

The glycoconjugates of the present invention may be generally represented by the general formula P—(S)x-Gal wherein P is a peptide residue of a human serum glycoprotein and S is a sugar residue of a human serum glycoprotein, "x" is an integer from 1 to 100, and Gal is galactose residue. The glycoconjugates may be partially or completely asialylated. Especially useful glycoconjugates include fetuins, orosomucoids and asialoorosomucoids. The methods of the present invention allow cells such as stem cells to be targeted to such target tissues as the heart, the liver, the kidneys and the lungs, among others.

The glycoconjugates may be administered to the mammal in any time frame relative to administering the cell. They may be administered before, after or simultaneously with the administration of the cell. In a typical embodiment, the glycoconjugates are administered prior to the cell. The glycoconjugates and the cell may be administered in any suitable route. In some embodiments, they are administered parenterally or intravenously to the mammal.

The methods according to the present invention are also useful for targeting a gene of interest to a tissue in a mammal by introducing a cell naturally containing, or a cell transformed with, a gene of interest to the mammal. Such methods are useful for treating a disease characterized by a deficiency in a gene product in a mammal by administering a cell comprising a functional gene encoding the gene product into the mammal and administering a glycoconjugate to the mammal. According to these methods, a cell containing an exogenous functional gene of interest may be administered and localized to a particular organ in the body where it can function to produce a deficient gene product.

Also, the methods according to the present invention are useful for treating a disease characterized by tissue damage in a mammal by administering a cell and administering a glycoconjugate to the mammal. Because stem cells have the potential to generate replacement cells for a broad array of tissues and organs, such as the heart, the pancreas, and the nervous system, stem cells may be targeted to particular organs in the body to repair or replace cells or tissues that are damaged or destroyed by many devastating diseases and disabilities. In some embodiments, the disease may be a heart disease, a lung disease, a kidney disease, or a liver disease, such as, for example, myocardial infarction, emphysema, cystic fibrosis, microalbuminuria, stroke, or hepatitis.

The methods according to the present invention are also useful for treating a disease characterized by tissue damage in a mammal by administering a glycoconjugate to the mammal and administering chemicals or biopharmaceuticals that mobilize stem cells into the circulation. The concentration of circulating mobilized stem cells may be limited because certain organs may sequester stem cells, thereby limiting delivery of an effective dose to the damaged organ. By inhibiting sequestration, the glycoconjugates of the invention increase the cell dose at the organ, thereby increasing the potential to generate replacement cells. The methods can be used for a broad array of tissues and organs, such as the heart, the pancreas, and the nervous system. Stem cells may be targeted to particular organs in the body to repair or replace cells or tissues that are damaged or destroyed by many devastating diseases and disabilities. In some embodiments, the disease may be a heart disease, a lung disease, a kidney disease, a neurological disease, or a liver disease, such as, for example, myocardial infarction, emphysema, cystic fibrosis, microalbuminuria, stroke, or hepatitis.

In other embodiments, the present invention provides pharmaceutical compositions comprising a cell and a glycoconjugate, e.g., glycoprotein. Glycoproteins useful in the present invention include, for example, fetuins, orosomucoids (O), and asialoorosomucoids (ASO). In other aspects, the present invention features kits for treating tissue damage or for delivering a functional gene or gene product to a tissue in a mammal comprising a cell and a glycoprotein. Glycoproteins useful in the invention include fetuins, orosomucoids, and asialoorosomucoids.

DETAILED DESCRIPTION OF THE INVENTION

A. Introduction

Figure 1:
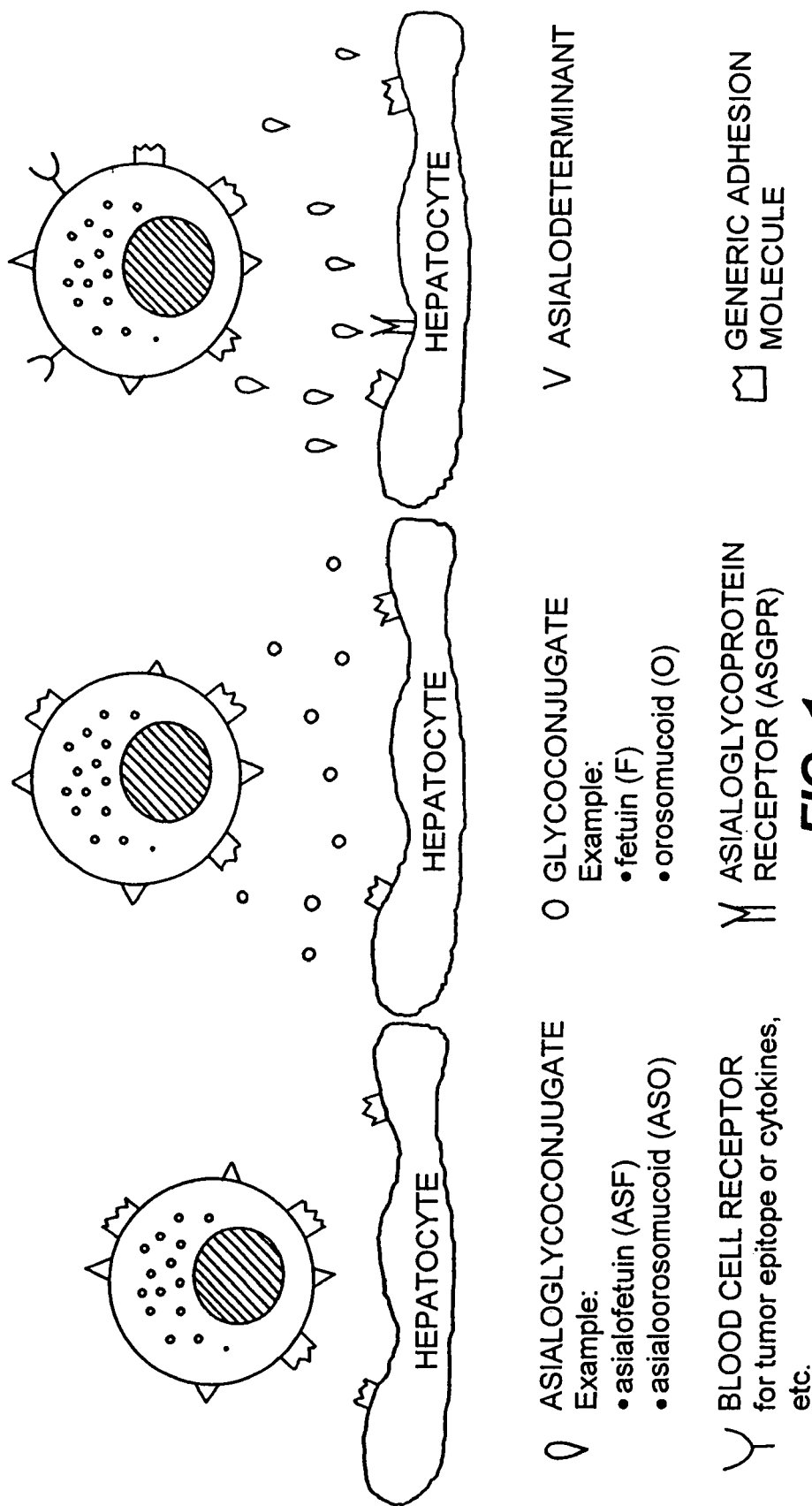
FIG. 1 provides a schematic of liver entrapment of bone marrow stem cells in the liver. Asialoglycodeterminants on the surface of cells react with asialoglycoprotein receptors on the surface of hepatocytes resulting in the localization of the bone marrow stem cells in the liver. Glycoconjugates including asialoglycoconjugates, block such interactions between asialoglycodeterminants on the surface of cells with asialoglycoprotein receptors on the surface of hepatocytes.

The present invention is directed to methods for delivering a cell to a target tissue in a mammal. The methods comprise the steps of administering, either simultaneously or sequentially, a carbohydrate-presenting molecule (i.e., a "glycoconjugate") and a cell to the mammal. In the methods of the present invention, glycoconjugates, especially asialoglycoconjugates, including asialo plasma proteins such as asialoorosomucoid (asialo alpha-(1)-acid glycoprotein), are thought to transiently bind the hepatic asialoglycoprotein receptor and thereby competitively inhibit attachment of cells bearing asialodeterminants from these receptors. Without wishing to be bound by theory, hyposialylated and desialyated proteins/glycoconjugates (also called asialoglycoconjugates) and cells which bear similar determinants are bound or "trapped" in the liver as a consequence of binding to the hepatic asialoglycoprotein receptors (see FIG. 1). Occupation of the receptor by the asialoglycoconjugate inhibits sequestration of the cells bearing similar determinants of interest in the liver.

In addition, the present disclosure shows that glycoconjugates of the invention prevent infused cells from concentrating in the alveolar vasculature. This finding suggests that lung sequestration of the cells may be related to expression of inflammatory receptors on endothelial cells, analogous to the reperfusion syndrome (see, e.g., Kilgore, et al., Cardiovasc. Res., vol. 28:437-444 (1994), and Eror, et al., Clin. Immunol., vol. 90:266-275 (1999)). This is supported by reports that orosomucoid, ASO, and agalacto/asialo-orosomucoid inhibit neutrophil activation superoxide anion generation, as well as platelet activation, as noted above.

The present invention further demonstrates that the glycoproteins may be used to traffic or target cells to particular organs of the body by altering the particular glycoconjugate administered. The present methods are useful to improve the efficacy of bone marrow and stem cell transplants, tissue repair, or gene therapy.

In embodiments wherein the cell is targeted to the lungs, the methods feature administering the cell to the mammal in a saline or serum albumin-saline solution. In some embodiments wherein the hematopoietic stem cell is targeted to the heart, the methods feature administering an asialoorosomucoid, and administering the cell to the mammal. In other embodiments wherein the mesenchymal stem cell is targeted to the heart, the methods feature administering an orosomucoid, and administering the cell to the mammal. In embodiments wherein the hematopoietic stem cell is targeted to the liver, the methods feature administering an orosomucoid and administering the cell to the mammal. In other embodiments wherein the mesenchymal stem cell is targeted to the liver, the methods feature administering an asialoorosomucoid and administering the cell to the to the mammal. In some embodiments, the orosomucoid or asialoorosomucoid is administered in at least two infusions prior to administering the cell to the mammal. The methods according to the present invention are also useful for inhibiting sequestration of a cell in the liver of a mammal even in the absence of targeting the cell to a target organ.

Asialoglycoconjugates, for example, asialofetuin and other asialo plasma proteins, are able to bind to the hepatic parenchymal and Kupffer cell asialoglycoprotein receptors. Blocking these receptors from binding and trapping cells bearing asialodeterminants, such as bone marrow cells, facilitates and increases the interval of their systemic circulation. In the case of bone marrow stem cells the administration of these compounds prevents the loss and destruction of bone marrow stem cells and increases the efficiency of engraftment. Bone marrow cells have cell surface asialodeterminants capable of binding to the asialoglycoprotein receptor, and this binding can be inhibited by the application of asialoglycoproteins.

The present invention takes advantage of the observation that when human peripheral hematopoietic stem (CD34+) cells or mesenchymal stem cells are infused into the jugular vein of immunodeficient mice, they localize predominantly in the lungs. When the cells are preceded by an infusion of asialoorosomucoid, the hematopoietic stem cells predominantly localize in the heart, whereas the mesenchymal stem cells localize in the liver. Alternately, when the cells are preceded by an infusion of orosomucoid (O), the hematopoietic stem cells localize in the liver, whereas the mesenchymal stem cells predominantly localize in the heart.

These protein infusions cause a more quantitative localization into the specific organs than occurs without them. Furthermore, hematopoietic stem cells that localize in the heart due to the influence of asialoorosomucoid leave the vascular space and are observed among the cardiac muscle cells by one hour after infusion. Moreover, once in the tissue, these cells lose their CD34 antigen, indicating that they are in the process of differentiating into cardiomyocytes. Additionally, at one hour CD34+ cells have been demonstrated to move from the vasculature into lung tissue. In an orosomucoid-treated mouse, clusters of stem cells are found in the liver parenchyma and are also demonstrated to lose their CD34 antigen, again suggesting differentiation into hepatocytes.

The present invention demonstrates the ability to direct high concentrations of stem cells to a specific organ in an atraumatic manner. This enhances the probability and the rate at which stem cells migrate into a target tissue and differentiate into the desired cell type. The present invention utilizes the observation that delivery of orosomucoid or ASO to the vessel proximal to the heart causes transfused stem cells to accumulate in the heart. Without wishing to be bound by theory, the effect may be caused by the glycoprotein infusion sensitizing the endothelium directly downstream from the infusion site, which causes the endothelial cells to bind stem cells and enhance their migration across the endothelium into the tissue.

The present findings with glycoconjugates indicate that the majority of a stem cell transfusion can be concentrated in the target organ, thereby providing the means to deliver an effective regimen of cell doses. This offers an opportunity to noninvasively target solid organs such as the heart, thereby competing with invasive direct injection. Perhaps more importantly, glycoconjugates provide the means to target very diffuse tissues, such as the liver and the kidney, which are not amenable to dosage by injection.

It is recognized that hematopoietic stem cells (HSC) recovered from the marrow, peripheral blood or umbilical cord blood and mesenchymal stem cells (MSC) recovered as marrow stromal cells, stromal cells from liposuction fat, or proliferated from stationary stromal progenitor cells in cord blood-depleted expelled placentas appear to be almost interchangeable in their differentiation ability, and act as multipotent stem cells.

Such cells have been shown to differentiate into functional cells when localized in specific organs and tissues: hepatocytes and cholangiocytes in the liver; cardiac muscle cells and arterial smooth muscle cells and endothelial cells in the heart; pneumocytes I and II in alveoli and bronchial epithelium in the lungs; chondrocytes for cartilage restoration; and intestinal mucosal cells, etc.

B. Stem Cells

Stem cells may hold the key to replacing cells lost in many devastating diseases such as Parkinson's disease, diabetes, acute and chronic heart disease, end-stage kidney disease, liver failure, and cancer. For many diseases, there are no effective treatments but the goal is to find a way to replace what natural processes have taken away.

To date, published scientific papers indicate that adult stem cells have been identified in brain, bone marrow, peripheral blood, blood vessels, skeletal muscle, epithelia of the skin and digestive system, cornea, dental pulp of the tooth, retina, liver, and pancreas. Thus, adult stem cells have been found in tissues that develop from all three embryonic germ layers.

By way of definition, the following terms are understood in the art:

A "stem cell" is a cell from the embryo, fetus, or adult that has, under certain conditions, the ability to reproduce itself for long periods or, in the case of adult stem cells, throughout the life of the organism. It also can give rise to specialized cells that make up the tissues and organs of the body.

A "pluripotent stem cell" has the ability to give rise to types of cells that develop from the three germ layers (mesoderm, endoderm, and ectoderm) from which all the cells of the body arise. The only known sources of human pluripotent stem cells are those isolated and cultured from early human embryos and from fetal tissue that was destined to be part of the gonads.

An "embryonic stem cell" is derived from a group of cells called the inner cell mass, which is part of the early (4- to 5-day) embryo called the blastocyst. Once removed from the blastocyst the cells of the inner cell mass can be cultured into embryonic stem cells. These embryonic stem cells are not themselves embryos.

An "adult stem cell" is an undifferentiated (unspecialized) cell that occurs in a differentiated (specialized) tissue, renews itself, and becomes specialized to yield all of the specialized cell types of the tissue in which it is placed when transferred to the appropriate tissue. Adult stem cells are capable of making identical copies of themselves for the lifetime of the organism. This property is referred to as "self-renewal." Adult stem cells usually divide to generate progenitor or precursor cells, which then differentiate or develop into "mature" cell types that have characteristic shapes and specialized functions, e.g., muscle cell contraction or nerve cell signalling. Sources of adult stem cells include bone marrow, blood, the cornea and the retina of the eye, brain, skeletal muscle, dental pulp, liver, skin, the lining of the gastrointestinal tract, and pancreas.

Stem cells from the bone marrow are the most studied type of adult stem cells. Currently, they are used clinically to restore various blood and immune components to the bone marrow via transplantation. There are currently identified two major types of stem cells found in bone marrow: hematopoietic stem cells (HSC, or CD34+ cells) which are typically considered to form blood and immune cells, and stromal (mesenchymal) stem cells (MSC) that are typically considered to form bone, cartilage, muscle, and fat. However, both types of marrow-derived stem cells recently have demonstrated extensive plasticity and multipotency in their ability to form the same tissues.

The marrow, located in the medullary cavity of bones, is the sole site of hematopoiesis in adult humans. It produces about six billion cells per kilogram of body weight per day. Hematopoietically active (red) marrow regresses after birth until late adolescence after which time it is focused in the lower skull vertebrae, shoulder and pelvic girdles, ribs, and sternum. Fat cells replace hematopoietic cells in the bones of the hands, feet, legs and arms (yellow marrow). Fat comes to occupy about fifty percent of the space of red marrow in the adult and further fatty metamorphosis continues slowly with aging. In very old individuals, a gelatinous transformation of fat to a mucoid material may occur (white marrow). Yellow marrow can revert to hematopoietically active marrow if prolonged demand is present such as with hemolytic anemia. Thus, hematopoiesis can be expanded by increasing the volume of red marrow and decreasing the development (transit) time from progenitor to mature cell.

The marrow stroma consists principally of a network of sinuses that originate at the endosteum from cortical capillaries and terminate in collecting vessels that enter the systemic venous circulation. The trilaminar sinus wall is composed of endothelial cells, an underdeveloped, thin basement membrane, and adventitial reticular cells that are fibroblasts capable of transforming into adipocytes. The endothelium and reticular cells are sources of hematopoietic cytokines. Hematopoiesis takes place in the intersinus spaces and is controlled by a complex array of stimulatory and inhibitory cytokines, cell-to-cell contacts, and the effects of extracellular matrix components on proximate cells. In this unique environment, lymphohematopoietic stem cells differentiate into all of the blood cell types. Mature cells are produced and released to maintain steady-state blood cell levels. The system may meet increased demands for additional cells as a result of blood loss, hemolysis, inflammation, immune cytopenias, and other causes. The engraftment efficiency of bone marrow stem cells could be improved by preventing entrapment by the liver via the hepatic asialoglycoprotein receptor.

A "progenitor" or "precursor" cell occurs in fetal or adult tissues and is partially specialized; it divides and gives rise to differentiated cells. Researchers often distinguish precursor/ progenitor cells from adult stem cells in that when a stem cell divides, one of the two new cells is often a stem cell capable of replicating itself again. In contrast, when a progenitor/ precursor cell divides, it can form more progenitor/precursor cells or it can form two specialized cells. Progenitor/precursor cells can replace cells that are damaged or dead, thus maintaining the integrity and functions of a tissue such as liver or brain.

Means for isolating and culturing stem cells useful in the present invention are well known. Umbilical cord blood is an abundant source of hematopoietic stem cells. The stem cells obtained from umbilical cord blood and those obtained from bone marrow or peripheral blood appear to be very similar for transplantation use. Placenta is an excellent readily available source for mesenchymal stem cells. Moreover, mesenchymal stem cells have been shown to be derivable from adipose tissue and bone marrow stromal cells and speculated to be present in other tissues. While there are dramatic qualitative and quantitative differences in the organs from which adult stem cells can be derived, the initial differences between the cells may be relatively superficial and balanced by the similar range of plasticity they exhibit. For instance, adult stem cells both hematopoietic and mesenchymal, under the appropriate conditions can become cardiac muscle cells. Delineation of full range of potential for adult stem cells has just begun.

Stem cells may be isolated for transduction and differentiation using known methods. For example, in mice, bone marrow cells are isolated by sacrificing the mouse and cutting the leg bones with a pair of scissors. Stem cells may also be isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells). For an example of this protocol, see Inaba, et al., J. Exp. Med., vol. 176:1693-1702(1992).

In humans, CD34+ hematopoietic stem cells can be obtained from a variety of sources, including cord blood, bone marrow, and mobilized peripheral blood. Purification of CD34+ cells can be accomplished by antibody affinity procedures. An affinity column isolation procedure for isolating CD34+ cells is described by Ho, et al., Stem Cells, vol. 13 (suppl. 3): 100-105(1995). See also, Brenner, Journal of Hematotherapy, vol. 2:7-17 (1993). Methods for isolating, purifying, and culturally expanding mesenchymal stem cells are known. Specific antigens for MSC are also known (see, e.g., U.S. Pat. Nos. 5,486,359 and 5,837,539).

C. Carbohydrate Presenting Molecules

The carbohydrate-presenting molecules useful in the present invention can be any molecule capable of presenting the appropriate carbohydrate structure that leads to enhancing or inhibiting the targeting of the cell of interest to a target tissue. The targeting function can be carried out using a carbohydrate molecule such as an oligosaccharide, polysaccharide, or the carbohydrate structure can be bound to larger molecule or carrier, referred to here as a glycoconjugate. Typically, the carbohydrate molecule will be linked to either a naturally occurring carrier (e.g., as part of a glycoprotein or glycolipid) or the carrier may be synthetic (e.g., an engineered polypeptide sequence). One of skill will recognize that a number of carriers can be used to present the appropriate structure. Examples of appropriate carrier molecules include polypeptides, lipids, and the like. Preparation and use of targeted compounds using asialo carbohydrate moieties is described in the art (see, e.g., U.S. Pat. Nos. 5,679,323, 5,089, 604, 5,032,678, and 5,284,646). One of skill will recognize that such compounds can also be used as carbohydrate presenting molecules useful in the present invention.

Figure 2:
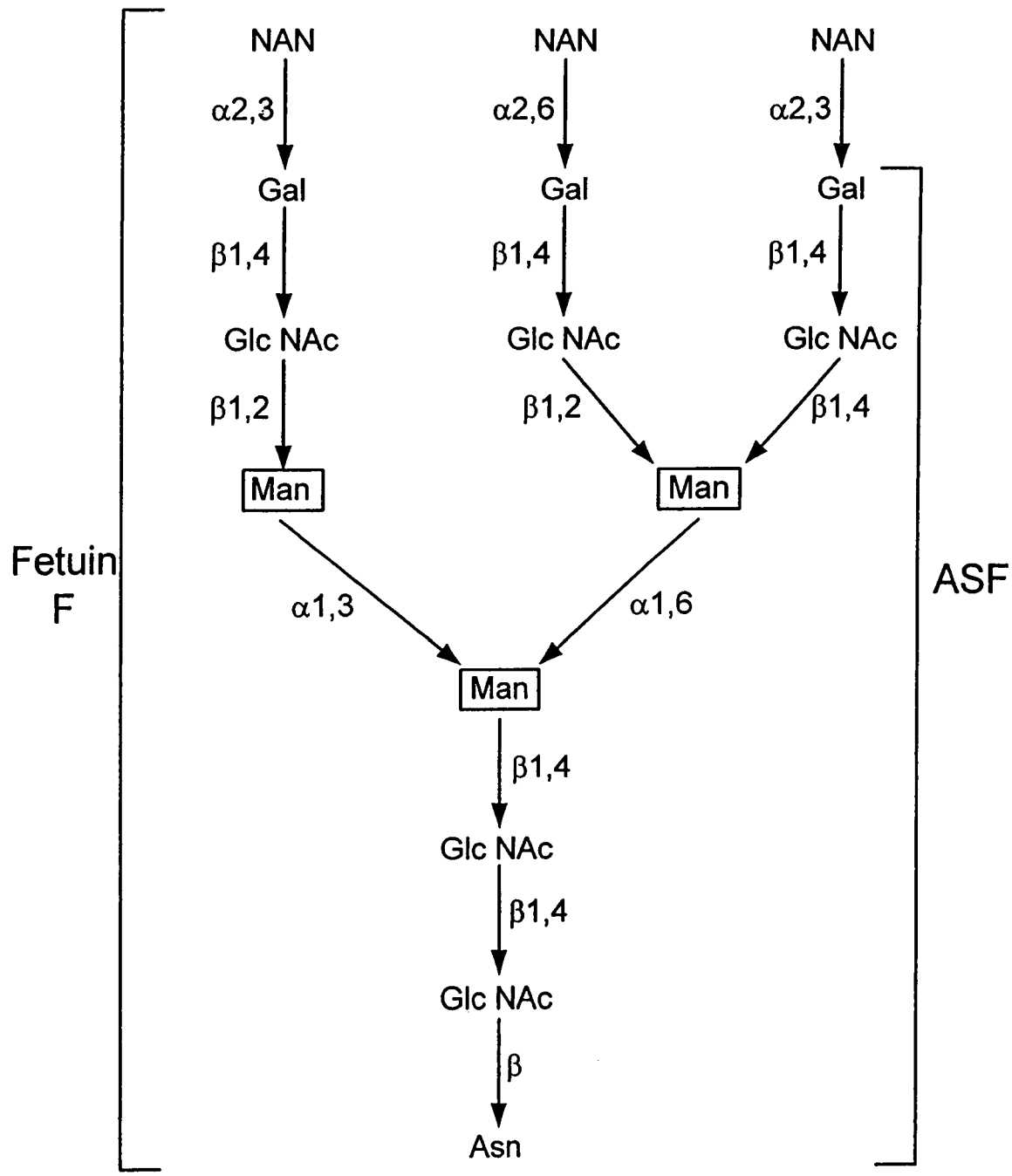
FIG. 2 shows the carbohydrate structure on two exemplary glycoproteins of the invention.

In cases in which the glycoconjugate is a glycoprotein it may be generally represented by the general formula P—(S) x-Gal, wherein "P" is a peptide residue of a human serum glycoprotein and "S" is a sugar residue of a human serum glycoprotein, "x" is an integer from 1 to 100, and "Gal" is a galactose residue. Especially useful glycoconjugates include fetuins and asialofetuins (see FIG. 2), orosomucoids and asialoorosomucoids, and galactose-bonded polylysine, galactose-bonded polyglucosamine, and the like.

The methods of the present invention allow cells such as stem cells to be targeted to such target tissues as the heart, the liver, the kidneys, and the lungs, among others. Parenteral administration of a glycoconjugate, such as asialoorosomucoid, may be used to block the hepatic asialoglycoprotein receptor and allow the cells bearing surface asialodeterminants (for example, peanut agglutinin (PNA)+ cells) to continue to circulate and migrate to the marrow space. Asialoorosomucoid is one of the glycoproteins that has been shown to bind to the hepatic asialoglycoprotein receptor and has been extensively used to characterize this receptor.

Figure 3:
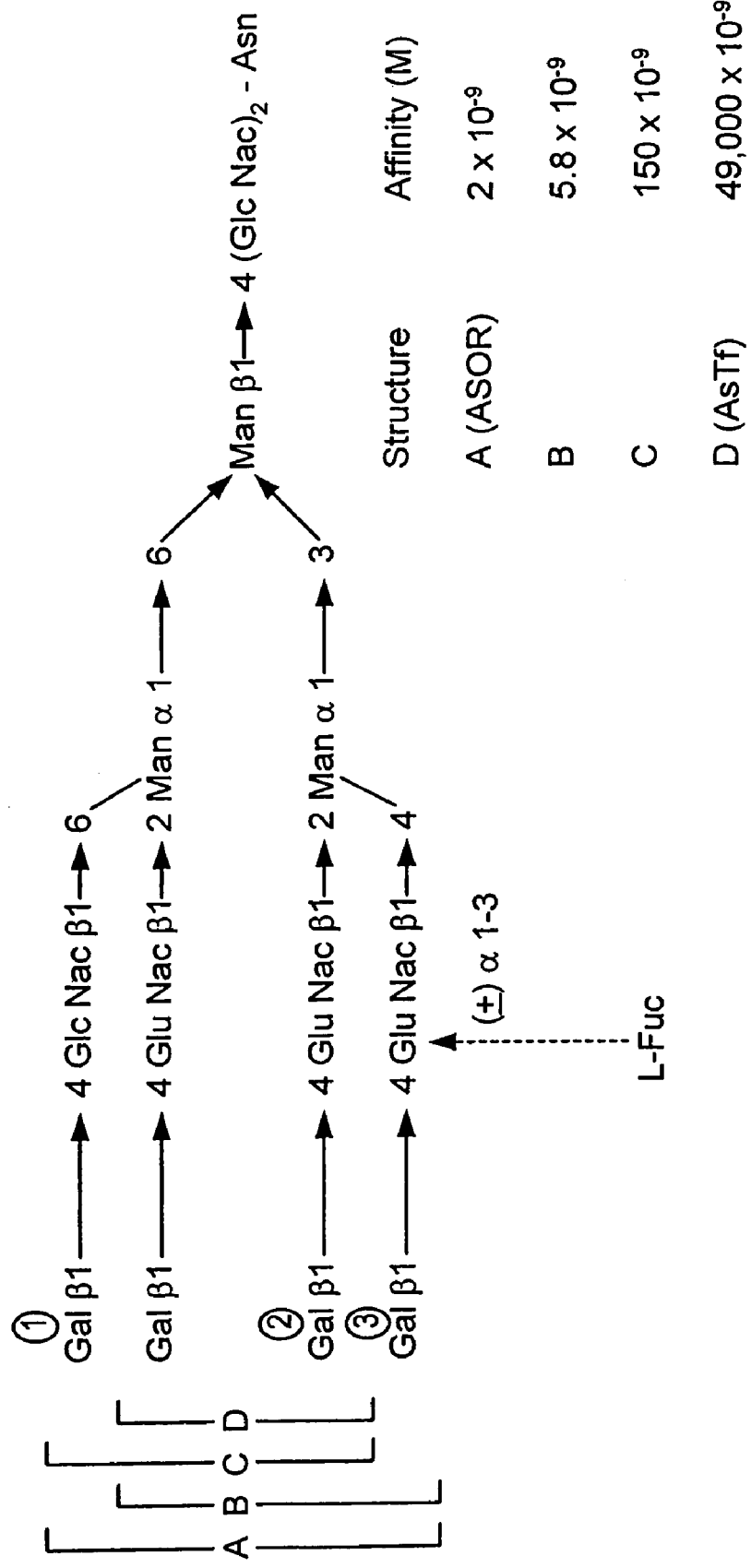
FIG. 3 shows the relative binding affinities of different carbohydrates for the asialoglycoprotein receptor.
Figure 4:
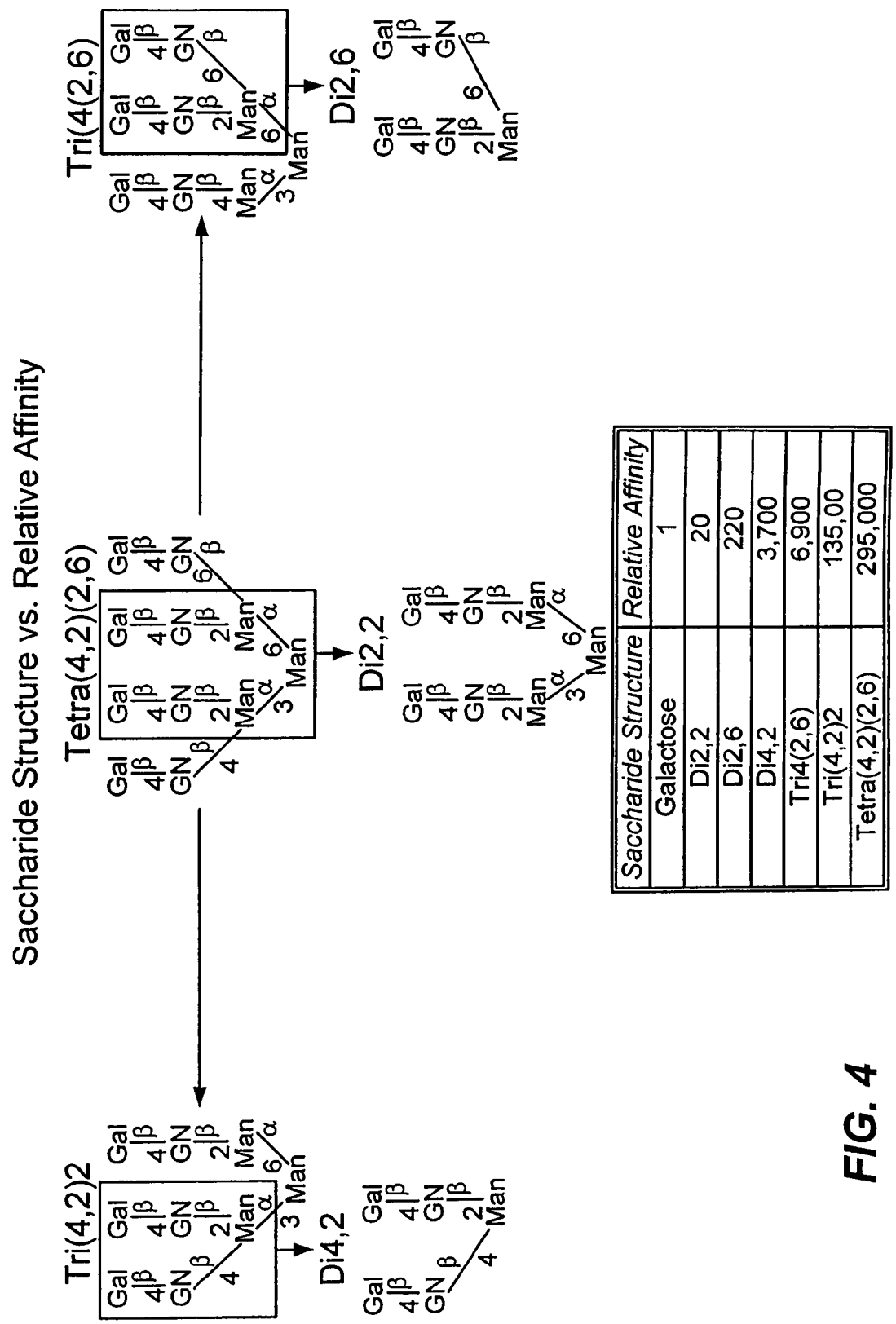
FIG. 4 shows the relative binding affinities of different carbohydrates for the asialoglycoprotein receptor.

Different compounds have different binding affinities for the asialoglycoprotein receptor, depending upon the carbohydrate presented (see, FIGS. 3 and 4). Thus, one of skill can modulate cell targeting by using compounds that present different carbohydrate structures.

Intravenous administration of a glycoconjugate, especially an asialoglycoprotein such as asialoorosomucoid, may be used to block the hepatic asialoglycoprotein receptor and allow the cells bearing surface asialodeterminants to continue to circulate and migrate to the marrow space or to the organ of interest. The glycoconjugates may be administered to the mammal in any time frame relative to the cells, but in some embodiments, the glycoconjugates are administered prior to administering the cell. The asialoglycoconjugates and the cell may be administered in any suitable route, but in some embodiments, they are administered intravenously to the mammal, and in other embodiments, they are administered parenterally. In embodiments wherein the cell is targeted to the lungs, the methods feature administering the cell to the mammal in a saline or serum albumin-saline solution. In some embodiments wherein the hematopoietic stem cell is targeted to the heart, the methods feature administering an asialoorosomucoid and administering the cell to the mammal. In other embodiments wherein the mesenchymal stem cell is targeted to the heart, the methods feature administering an orosomucoid and administering the cell to the mammal. In embodiments wherein the hematopoietic stem cell is targeted to the liver, the methods feature administering an orosomucoid and administering the cell to the mammal. In other embodiments wherein the mesenchymal stem cell is targeted to the liver, the methods feature administering an asialoorosomucoid and administering the cell to the to the mammal. In some embodiments, the orosomucoid or asialoorosomucoid is administered in at least two infusions, prior to and after administering the cell to the mammal. The methods according to the present invention are also useful for inhibiting sequestration of a cell in the liver of a mammal even in the absence of targeting the cell to a target organ.

The alpha-(1)-acid glycoprotein (orosomucoid or AAG) is a normal constituent of human plasma (650±215 µg/ml) that increases in concentration as much as five-fold in association with acute inflammation and cancer, and thus is recognized as an acute phase protein. Orosomucoid consists of a single polypeptide chain, has a molecular weight of 44,100, and contains approximately 45% carbohydrate including 12% sialic acid. It is the most negatively charged of the plasma proteins. Certain of the biological properties of orosomucoid are related to its sialic acid content. Thus, clearance and immunogenicity of orosomucoid are markedly increased on desialylation. The biological functions of orosomucoid are largely unknown. Orosomucoid has the ability to inhibit certain lymphocyte reactivities including blastogenesis in response to concanavalin A, phytohaemagglutinin and allogeneic cells, and these inhibitory effects are enhanced in association with desialylation. It has been reported that unphysiologically large (5-15 mg/ml) amounts of orosomucoid inhibit the platelet aggregation induced by ADP and adrenaline, and there is evidence that a sialic acid-deficient species of orosomucoid appears elevated in several chronic disease states.

D. Gene Therapy

The present invention is also directed to using living cells to deliver therapeutic genes into the body. In some embodiments, the therapeutic gene is a transgene. For example, the delivery cells—a type of stem cell, a lymphocyte, or a fibroblast—are removed from the body, and a therapeutic transgene is introduced into them via vehicles well known to those skilled in the art such as those used in direct gene transfer methods. While still in the laboratory, the genetically modified cells are tested and then allowed to grow and multiply and, finally, are infused back into the patient. Alternatively, allogeneic cells that bear normal, endogenous genes can reverse a deficiency in a particular target tissue. Use of cells bearing either transgenes or normal, endogenous genes is referred to herein as gene therapy.

Gene therapy using genetically modified cells offers several unique advantages over direct gene transfer into the body. First, the addition of the therapeutic transgene to the delivery cells takes place outside the patient, which allows the clinician an important measure of control because they can select and work only with those cells that both contain the transgene and produce the therapeutic agent in sufficient quantity.

Of the stem cell-based gene therapy trials that have had a therapeutic goal, approximately one-third have focused on cancers (e.g., ovarian, brain, breast myeloma, leukemia, and lymphoma), one-third on human immunodeficiency virus disease (HIV-1), and one-third on so-called single-gene diseases (e.g., Gaucher's disease, severe combined immune deficiency (SCID), Fanconi anemia, Fabry disease, and leukocyte adherence deficiency).

In view of the foregoing, the methods according to the present invention are useful for targeting a gene of interest (either a transgene or an endogenous gene) to a tissue in a mammal by introducing a cell comprising the gene of interest and administering a glycoconjugate to the mammal. Such methods are useful for treating a disease characterized by a deficiency in a gene product in a mammal by administering a cell comprising a functional gene encoding the gene product into the mammal and administering a glycoconjugate to the mammal. Stem cells may be used as a vehicle for delivering genes to specific tissues in the body. Stem cell-based therapies are a major area of investigation in cancer research.

The current invention provides localizing of transfused cells such as stem cells to provide a functional gene to a patient suffering from a disease caused by a lack of that gene. In many instances of genetically based diseases, a low level production of that gene product will effectively ameliorate or cure the disease. By providing the gene that is deficient through transfusion of stem cells from a normal donor into the patient, the stem cells may be directed to localize in an organ or tissue of choice, causing a microchimerization of that patient in that organ or tissue, from which organ or tissue that gene product can be delivered to the patient. Therefore, the present invention provides the ability to direct the localization of the transfused cells such as allogeneic stem cells that have a stable, normal gene. Such transfused cells then create a stable micro-chimera of the recipient.

Those of skill in the art are aware of the genetic deficiencies causative of a large array of genetically based diseases. Exemplary genes and diseases that can be treated include CTFR protein in cystic fibrosis and proteins associated with coagulopathy in the liver. For example, treatment of Hemophilia A can be accomplished using gene therapy. In such embodiment, a transfusion of such cells as umbilical cord blood hematopoietic stem cells may be administered to deliver an intact normal Factor VIII gene. Alternatively, transformed cells can comprise a normal, wild-type Factor VIII gene. Such cells carrying a functional Factor VIII gene may be directed to localize in the liver, preferably by orosomucoid or asialoorosomucoid perfusion prior to the infusion of the stem cells. The cells transform into hepatocytes and begin secreting Factor VIII into the blood.

Other embodiments of gene therapy according to the present invention include treating Hemophilia B (Factor IX deficiency), and antithrombin III, Protein C, and Protein S deficiencies. While these diseases all involve the blood coagulation system, gene therapy may include treating different tissues, such as muscular dystrophy, cystic fibrosis, and the like.

E. Introducing Transgenes into Stem Cells

Means for introducing transgenes into cells are well known. A variety of methods for delivering and expressing a nucleic acid within a mammalian cell are known to those of ordinary skill in the art. Such methods include, for example, viral vectors, liposome-based gene delivery (WO 93/24640; Mannino Gould-Fogerite, BioTechniques, vol. 6(7):682-691 (1988); U.S. Pat. No. 5,279,833; WO 91/06309; Felgner, et al., Proc. Natl. Acad. Sci. USA, vol. 84:7413-7414 (1987); and Budker, et al., Nature Biotechnology, vol. 14(6):760-764 (1996)). Other methods known to the skilled artisan include electroporation (U.S. Pat. Nos. 5,545,130, 4,970,154, 5,098,843, and 5,128,257), direct gene transfer, cell fusion, precipitation methods, particle bombardment, and receptor-mediated uptake (U.S. Pat. Nos. 5,547,932, 5,525,503, 5,547,932, and 5,460,831). See also U.S. Pat. No. 5,399,346.

Widely used retroviral vectors include those based upon murine leukemia virus (MuLV), gibbon ape leukemia virus (GaLV), Simian Immunodeficiency virus (SIV), human immunodeficiency virus (HIV), and combinations thereof. See, e.g., Buchscher, et al., J. Virol., vol. 66(5):2731-2739 (1992); Johann, et al., J. Virol., vol. 66(5):1635-1640 (1992); Sommerfelt, et al., Virol., vol. 176:58-59 (1990); Wilson, et al., J. Virol., vol. 63:2374-2378 (1989); Miller, et al., J. Virol., vol. 65:2220-2224 (1991); PCT/US94/05700, and Rosenburg and Fauci, in Fundamental Immunology, Third Edition (Paul ed., 1993)).

AAV-based vectors are also used to transduce cells with target nucleic acids, e.g., in the in vitro production of nucleic acids and polypeptides, and in vivo and ex vivo gene therapy procedures. See West, et al., Virology, vol. 160:38-47 (1987); U.S. Pat. No. 4,797,368; WO 93/24641; Kotin, Human Gene Therapy, vol. 5:793-801 (1994); Muzyczka, J. Clin. Invest., vol. 94:1351 (1994), and Samulski (supra) for an overview of AAV vectors. Construction of recombinant AAV vectors are described in a number of publications, including Lebkowski, U.S. Pat. No. 5,173,414; Tratschin, et al., Mol. Cell. Biol., vol. 5(11):3251-3260 (1985); Tratschin, et al., Mol. Cell. Biol. Vol. 4:2072-2081 (1984); Hermonat and Muzyczka, Proc. Natl. Acad. Sci., USA, vol. 81:6466-6470 (1984); and Samulski, et al., J Virol., vol. 63:03822-3828 (1989).

Retroviral vectors are typically used for cells useful in the present invention. Such vectors may comprise, for example, an HIV-2 packageable nucleic acid packaged in an HIV-2 particle, typically using a packaging cell line. Cell transduction vectors have considerable commercial utility as a method of introducing genes into target cells. In particular, gene therapy procedures, in which the cell transduction vectors of the invention are used to transduce target cells with a therapeutic nucleic acid in an in vivo or ex vivo procedure, may be used. Gene therapy provides a method for combating chronic diseases caused by a gene deficiency, infectious diseases such as HIV, as well as non-infectious diseases such as cancer.

Stem cells such as CD34+ stem cells may be used in ex vivo procedures for cell transduction and gene therapy. The present invention utilizes the feature that stem cells differentiate into other cell types in vitro, or can be introduced into a mammal (such as the donor of the cells) where they will engraft in the bone marrow unless targeted to another organ for differentiation. Hence, the present invention extends to directing stem cells to particular organs to regenerate tissue such as to the heart to regenerate cardiac muscle cells, to the lung to regenerate alveoli, and to the kidneys to regenerate tissue and to directing cells such as CD34+ stem cells to an organ to ameliorate a genetic abnormality by providing efficacious amounts of a deficient gene product. Methods for differentiating CD34+ cells in vitro into clinically important immune cell types using cytokines such a GM-CSF, IFN-γ and TNF-α are known (see Inaba, et al., J. Exp. Med., vol. 176, 1693-1702(1992), and Szabolcs, et al., 154:5851-5861 (1995)). Yu, et al. (Proc. Natl. Acad. Sci., USA, vol. 92:699-703(1995)) describe a method of transducing CD34+ cells from human fetal cord blood using retroviral vectors.

F. Pharmaceutical Compositions

In other embodiments, the present invention provides pharmaceutical compositions comprising a cell and a glycoconjugate of the invention. Exemplary glycoproteins include orosomucoids and asialoorosomucoids. In other aspects, the present invention features kits for treating tissue damage or for delivering a functional gene or gene product to a tissue in a mammal comprising a cell and a glycoprotein. Stem cells generally have been presented to the desired organs either by injection into the tissue, by infusion into the local circulation, or by mobilization of autologous stem cells from the marrow accompanied by prior removal of stem cell-entrapping organs before mobilization when feasible, e.g., splenectomy.

Glycoconjugates may be administered prior to, concomitantly with, or after infusing the stem cells. In some embodiments, an intravenous fluid bag may be used to administer the glycoconjugate in a saline or dextrose solution with and without protein, or serum-free media, including, but not restricted to, RPMI 1640 or AIM-V. In such embodiments, the glycoconjugate may be mixed with the cells in the same bag or in a "piggy-back". The glycoconjugate may also be continued after administration of the cells to permit longer systemic circulation times or increased specific organ accumulation. This procedure may be repeated as often as needed for delivering a therapeutic dose of the cells to the target organ. The preparation may be used with little concern for toxicity given data from animal studies demonstrating no side effects at doses of 3-7 mg of glycoconjugate per ml of blood volume.

Administration of cells transduced ex vivo can be by any of the routes normally used for introducing a cell or molecule into ultimate contact with blood or tissue cells. The transduced cells may be administered in any suitable manner, preferably with pharmaceutically acceptable carriers. Suitable methods of administering such cells in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there are a wide variety of suitable formulations of pharmaceutical compositions of the present invention.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration is one useful method of administration. The formulations can be presented in unit-dose or multi-dose sealed containers, such as ampules and vials, and in some embodiments, can be stored in a freeze-dried (lyophilized) condition requiring only the addition of the sterile liquid carrier, for example, water, for injections, immediately prior to use. These formulations may be administered with factors that mobilize the desired class of adult stem cells into the circulation.

Extemporaneous injection solutions and suspensions can be prepared from sterile powders, granules, and tablets of the kind previously described. Cells transduced by the vector as described above in the context of ex vivo therapy can also be administered parenterally as described above, except that lyophilization is not generally appropriate, since cells are destroyed by lyophilization.

The dose administered to a patient, in the context of the present invention should be sufficient to effect a beneficial therapeutic response in the patient over time. The dose will be determined by the efficacy of the particular cells employed and the condition of the patient, as well as the body weight of the patient to be treated. The size of the dose also will be determined by the existence, nature, and extent of any adverse side effects that accompany the administration of a cell type in a particular patient. In determining the effective amount of cells to be administered in the treatment or prophylaxis of diseases, the physician should evaluate circulating plasma levels, and, in the case of replacement therapy, the production of the gene product of interest.

Transduced cells are prepared for reinfusion according to established methods. See, e.g., Abrahamsen, et al., J. Clin. Apheresis, vol. 6:48--53(1991); Carter, et al., J. Clin. Apheresis, vol. 4:113-117(1988); Aebersold, et al., J. Immunol. Methods, vol. 112:1-7(1988); Muul, et al., J. Immunol. Methods, vol. 101:171-181(1987), and Carter, et al., Transfusion, vol. 27:362-365(1987). After a period of about 2-4 weeks in culture, the cells may number between $1 \times 10^6$ and $1 \times 10^{10}$. In this regard, the growth characteristics of cells vary from patient to patient and from cell type to cell type. About 72 hours prior to reinfusion of the transduced cells, an aliquot is taken for analysis of phenotype and percentage of cells expressing the therapeutic agent.

For administration, cells of the present invention can be administered at a rate determined by the LD-50 of the cell type, and the side effects of the cell type at various concentrations, as applied to the mass and overall health of the patient. Administration can be accomplished via single or divided doses. Adult stem cells may also be mobilized using exogenously administered factors that stimulate their production and egress from tissues or spaces, that may include, but are not restricted to, bone marrow or adipose tissues. The exemplary glycoconjugates may be administered concurrently, prior to and/or following stem cells mobilization, or at a time when the amount of cells in the peripheral circulation is optimal for the desired therapeutic endpoint.

EXAMPLES

Procedures

Intravenous cannulas were placed into the external jugular vein of NOD-SCID mice under anesthesia (Institutional Animal Care and Use Committee protocol #AM87046-07) to enable the efficient delivery of $^{111}$In-labeled stem cells i.v. Tylenol elixir was administered by mouth after recovery from anesthesia. Briefly, radiolabelled CD34+ cells were taken up in 100-250 ul of 5% human plasma albumin in saline and injected into the cannula and then flushed with 50 ul of the albumin-saline. The mice were imaged by nuclear medicine.

Mice: NOD-SCID, female mice (non-obese diabetic/LtSz-scid/scid) were obtained from the Jackson Laboratory, Bar Harbor, Me. at 1-2 months of age. These animals were maintained in microisolator cages in a special isolator room. The air was HEPA filtered, and the animals were changed in a laminar flow hood within the facility. All food, bedding, and water was sterilized. NOD-SCID mice were ideally suited for the study of xenotransplanted tumors and hematopoietic cells and lymphocytes because of their immunoincompetence including greatly reduced NK activity. See, e.g. Hogan, et al., Biology of Blood & Marrow Transplantation, vol. 3:236-46 (1997); Noort, et al., Bone Marrow Transplantation, vol. 22 Suppl 1:S58-60 (1998).

All administrations of agents or cells were done either i.v. or i.p.

Stem Cells: CD34+ stem cells were isolated from apheresis stem cell collection products derived from deceased cancer patients. They were purified to 95-99% purity using antibody conjugated to CD34 conjugated to magnetics beads (MACS separation columns; Miltenyi Biotec, Auburn, Calif.) and cryopreserved.

Human mesenchymal stem cells (hMSCs; PT-2501) obtained through an FDA-monitored, paid bone marrow donor program were purchased from Poietics Technologies, BioWhittaker (Walkerville, Md.). The cells were thawed according to manufacturer recommendations, resuspended, and radiolabelled in Mesenchymal Stem Cell Basal Medium (MSCBM).

Proteins administered: Orosomucoid (alpha-1 acid glycoprotein) and asialoorosomucoid (ASO) were administered in the following buffer containing 0.16 mM Caprylate, 10 mM TRIS, 150 mM NaCl, pH 7.0.

Anesthesia and analgesia: A rodent anesthesia cocktail of 0.04 ml per 20-30 g mouse i.p. (Rodent Cocktail recipe: 1.5 ml of 50 mg/ml ketamine, plus 1.5 ml of 20 mg/ml xylazine, plus 0.5 ml of 50 mg/ml acepromazine) was used. The anesthetic agent, Rodent anesthesia cocktail, was administered i.p. as follows:
1) for surgery: 0.04 ml per 20-30 g mouse; and
2) for imaging: 0.02 ml per 20-30 g mouse.

Post-surgical Analgesia: Tylenol 60 ul/20 g mouse (6.10 mg) was administered by mouth after anesthesia had partially worn off. The analgesic agent was tylenol by mouth at 60 ul (6.10 mg) per 20 g mouse immediately after surgery or at the first signs of distress. Xylazine contained in an anesthetic formulation may also act as an analgesic.

Surgical procedure (standard cannula placement): After anesthetizing the animals as previously described, the threads for suturing a cannula filled with citrate saline were soaked in 70% ethanol. The anesthetized animals were secured with paper tape on the operating platform ventral side up. The area from just below the clavicle to the ear was shaved. The shaven area was cleaned with Betadine and rinsed with 70% ethanol. A vertical incision was made in the skin of the right neck from the top of the rib cage to the jaw bone to expose the sternocleidomastoid muscle with the external jugular vein just beneath. To clearly expose the operating field, the skin was retracted with wire hooks (secured to small weights). Retraction should not distort the underlying tissue but should stabilize the area for visualization and cannula insertion. The vein was cleared of overlying fat and fascia using microscopic forceps. The circulation in the superior vena cava was cut off using a half a knot of 4 O silk surgical sutures. One side of the thread was secured with a clamped hemostat. A second piece of thread was looped around the bottom of the vein to make a half knot without pulling it tight. This loop was used to secure the cannula once it had been inserted into the external jugular vein. The surface of the vein was nicked with the microscissors. The cannula was inserted into the vein with bevelled side up. The cannula was slid down diagonally until the anchor was flush with the wall of the vein and the lower knot tightened. The cannula was tested by pushing saline through it. The lower knot was finished after verifying no leakage. A full knot was tied around the cannula using the top thread. Saline flow in the cannula was monitored. The top thread was used to go under, catching tissues, and a knot was tied over the cannula again with this thread. A full knot was made using an end of the top thread and the bottom thread. This secured the superior and inferior threads over the hub of the cannula to prevent accidental dislodgement. The cannula was clamped off and the syringe removed. The cannula was positioned underneath the skin of the neck and exteriorized just below the occiput at the nape of the neck while rotating the animal (dorsal side up). An autoclip was used to staple the heat shrink part of the cannula in place near the exit. The cannula was cut to a reasonable length (1.5-2.0 inches), and a wire plug was placed into it. The animal was turned over to its original position and the neck closed with an autoclip, being careful not to puncture the cannula.

Surgical procedure (DaVinci Microport Vascular System cannula placement): The DaVinci Microport Vascular System (DaVinci Biomedical, South Lancaster, Mass.) is a closed injection route permitting its implantation up to 2 weeks prior to trafficking experiments without loss of patency. The essential difference is that the port is not externalized as before. This eliminates additional risk for contamination and damage to the cannula caused by chewing and scratching.

The incision area was cleaned with Betadine prior to initial cuts. The mouse was then taped (back side up) to the surgery board. An incision 3-4 mm was made. Next, the incision was made on the chest 4-5 mm. A tunnel was made from the back incision to the front incision in order to feed the cannula through the back to the chest. Heparin was pushed through the cannula. The cannula was then pulled through using hemostats. The skin was pulled loose from the tissue on the back for placement of the port. The port was sutured down to the tissue in the middle upper neck area. It was sutured in two places using a triple knot tie. Next, the mouse was turned on its back with its chest up. The cannula was then cut at an angle, where at least 1 mm and at most 2 mm of cannula was inserted in the jugular vein. The jugular vein was isolated in the chest after some fat and tissue was pulled away. The arms of the mice were taped down on their sides because that pushes the chest forward and further exposes the jugular vein. Once the jugular vein was isolated, two sutures were placed around it. The top of the vein was tied off enough to slow the flow of blood, but not to completely stop the flow. The lower tie was one to 2 mm from the top, and it was not tightened. The lower tie was used later to hold the cannula in place and to stop excessive bleeding from the jugular vein. Next, a small cut was made in the jugular vein between the two ties, so that the cannula could be fed into the vein. Once the cannula was placed in the vein the lower tie was tightened around the cannula within the vein. Next, the cannula was checked for leaks by running heparin through the cannula. After verifying no leaks, both incisions were closed.

$^{111}$Indium Oxine Labelling Procedure: $^{111}$In-oxine labelling of adult human CD34+ or mesenchymal stem cells (hMSCs) was performed using a modification of the Amersham Healthcare Procedure for labelling autologous leukocytes.

Harvesting for tissues for histopathology: Tissues were harvested after euthanasia. After the 1-hour image, the organs were harvested and half the organ was fixed in 10% neutral buffered formalin and the other half was frozen in OTC for frozen sections. The images presented herein are from fixed tissues.

Necropsy Procedure For Collection of Mouse Tissues: An initial midline skin incision from the anterior cervical region to the brim of the pubis was made followed by an abdominal incision following linea alba from the sternum to the pubis with a lateral reflection of the abdominal wall by incision following the caudal ribs. The sternum was reflected anteriorly by cutting the ribs at approximately the level of the costochrondral junction, incising the diaphragm and pericardium as needed. Anteriorly, reflection of sternum was extended to include the ventral cervical muscles to expose the trachea. The trachea and esophagus were incised at the mid cervical area and reflected caudally, cutting attachments as necessary to remove the thoracic viscera in toto. Following removal of the thoracic viscera, the entire heart was dissected free and immersed in 10% neutral buffered formalin. After immersion, the heart was massaged lightly with serrated tissue forceps to force fixative into the cardiac chambers. The trachea with attached lung was then immersed in fixative without further dissection. The spleen was visualized, omental attachments incised, removed, and immersed whole in formalin fixative. The stomach and intestinal tract were removed by incising the rectum and reflecting the viscera anteriorly while cutting attachments as necessary. The liver was removed in toto and immersed whole in formalin fixative. The kidneys were removed and immersed whole in formalin fixative. The pancreas was incised from the anterior duodenum and immersed in formalin fixative.

Trimming of Tissues for Paraffin Processing and Microtomy: The heart was placed on the trimming board with the right ventricle on the upperside and the left ventricle on the underside next to the trimming surface. A single upper-to-lower incision was made through the right ventricle and atrium and great vessels at the base of the heart continuing through the interventricular septum and the left cardiac chambers to achieve two approximately equal halves. Each half was placed into separate embedding cassettes containing fixative saturated foam pads and labelled "heart1" and "heart2". The entire left and right lungs were separated from midline tissues and placed flat on fixative-saturated foam pads in cassettes labelled "left" and "right" lung. Liver sections were taken from the right lateral and medial liver lobes and placed into an appropriately labelled cassette. The left lateral and medial lobes were sectioned and handled in a similar manner. The entire spleen was placed in an appropriately labelled embedding cassette and oriented with one long margin down, taking advantage of the curvature to increase initial sectional area. For one kidney, a whole coronal section was taken from the midpoint of the kidney. The remaining kidney was sectioned longitudinally. Both sections were placed in a single cassette. The collected pancreas was placed on formalin-saturated foam pad in an appropriately labelled cassette.

Imaging procedures: Nuclear Medicine. NOD-SCID mice were anesthetized using rodent anesthesia cocktail. Once anesthetized, the mice were placed on a foam hemi-cylindrical mouse-positioning device (MPD,) and covered with a tube sock. The MPD allows better visual separation of the lungs and liver as compared to placing the mouse on a flat surface. The foam on which the mouse was placed, and the tube sock covering maintained a comfortable temperature permitting longer imaging without additional anesthesia. The MPD was placed on a narrow table between the dual heads of a Siemens E.Cam Gamma Camera and imaged statically or dynamically in 2-D or SPECT. $^{57}$Co-Spot Marker is used to mark anatomic positions (nose, tail, cannula, etc.). The data was analyzed using a Siemens ICON system for regions of interest or percent of injected dose (e.g., liver, spleen, heart).

CT Imaging: A CT scan was performed (G.E. Medical System High Speed Spiral Tunnel) for tumor assessment and to enable the registration/alignment of the nuclear medicine image with that of the CT in order to determine precise location of injected radiolabelled stem cells using the method described by Arata L., Clinical Uses for Medical Image Registration: Experiences at Three Hospitals. Proceedings of PACMEDTec Symposium in Honolulu, Hi, Aug. 17-21, 1998. and Nelson, et al., Electromedica 68 (2000) 45-48. CT scans were performed during a nuclear medicine imaging session while the animals were under anesthesia. Anesthetized animals were transported to CT, either just prior to or immediately after, the nuclear medicine scan. Usually only one CT was done per animal. CT was used to precisely localize the radiolabelled materials anatomically, by fusing the CT image with that of the nuclear medicine SPECT images.

Gamma camera imaging using a Siemens E.Cam dual head gamma camera monitored the in vivo trafficking patterns of all human stem cells described in the following examples. Mice were placed on a Mouse Positioning Device (MPD) and placed between the detectors on the imaging platform.

Example 1

ASO Administered Intravenously Directs Human CD34+ to the Heart

Asialoorosomucoid (ASO)/High Dose HSC: When an infusion of $5.75 \times 10^6$ HSC was preceded by 3.3 mg ASO, 77±1% of the infused cells were found in the heart immediately after infusion, 75±5% remained in the heart region at 1.5 hr, decreasing to 52±1% at 24 hr.

$5.75 \times 10^6$, $^{111}$In-labeled human CD34+ (hCD34+) peripheral blood stem cells were administered intravenously (i.v.) via an external jugular vein cannula to 2 month old, NOD-SCID, female mice (Non-obese diabetic/LtSz-scid/scid) obtained from the Jackson Laboratory, Bar Harbor, Me. The radiolabelled CD34+ stem cells were administered after pretreatment of the mouse with 3.3 mg of asialoorosomucoid (ASO) i.v. The in vivo trafficking patterns were followed by gamma camera imaging using a Siemens E.Cam dual head gamma camera from immediately after injection up to 36 h post-infusion. Human CD34+ were isolated from apheresis stem cell collection products derived from deceased cancer patients. They were purified to 95-99% purity using antibody conjugated to CD34 conjugated to magnetics beads (MACS separation columns, Miltenyi Biotec, Auburn, Calif.) and cryopreserved.

Radiolabelled CD34+ stem cells administered after ASO migrated immediately to the heart. Anatomic localization was facilitated by the use of a $^{57}$Co-point source positioned at the level of the cannula. Up to 79.2% of the injected dose was located in the heart at 1.5 hours. These cells did not migrate to the liver and spleen early in the post-infusion follow up images but could be found in the liver later after 24 hours. However, 51.6-53.2% of the originally injected dose remained in the heart at 24 hours. At 36 hours imaging was conducted with the cannula in vivo and with the cannula removed and placed next to the sacrificed animal. These images show that the injected cells were not trapped in the cannula but were actually in the heart.

Example 2

Orosomucoid Administered Intravenously Enables Human CD34+ Cells to Migrate to the Liver and Spleen but not to the Heart Orosomucoid/High Dose HSC: When an infusion of $5.75 \times 10^6$ HSC was preceded by 5.5 mg orosomucoid, 74±3% of infused cells were found in the liver and spleen immediately after infusion, 74±4% of the cells remained in the liver region at 1.5 hr, decreasing to 63±1% at 24 hr.

The preparation and procedures set forth in Example 1 were repeated.

$5.75 \times 10^6$, $^{111}$In-labeled human CD34+ (hCD34+) peripheral blood stem cells were administered intravenously (i.v.) via an external jugular vein cannula to 2 month old, NOD-SCID, female mice (Non-obese diabetic/LtSz-scid/scid) obtained from the Jackson Laboratory, Bar Harbor, Me. The radiolabelled CD34+ stem cells were administered after pretreatment of the mouse with 5.5 mg of orosomucoid (O) i.v.

Mice were imaged and the biodistribution of the radiolabelled hCD34+ cells monitored as described in Example 1. Radiolabelled hCD34+ administered after O migrated immediately to the liver/spleen area and remained there until 36 hours. Anatomic localization was facilitated by the use of a $^{57}$Co-point source positioned at the level of the cannula. The localization to the liver/spleen region ranged from 76.3% immediately post-infusion to 63.6% at 24 hours. No $^{111}$In-labeled cells were found in the region of the heart.

At 36 hours imaging was conducted with the cannula in vivo and with the cannula removed and placed next to the sacrificed animal. These images show that the injected cells were not trapped in the cannula. Radioactivity was found at or below the cannula placement, i.e., in the region of the liver/spleen.

Example 3

Orosomucoid Enables hCD34+ Cells to Migrate to the Liver/Spleen without Significant Migration to the Heart Orosomucoid/Low Dose HSC: When an infusion of $0.5 \times 10^6$ HSC (one-tenth the previous cell dose) was preceded by 11 mg orosomucoid, 43±2% of infused cells were found in the liver and spleen immediately after infusion, and 40±3% of the cells remained in the liver region at 1 hr.

The preparation and procedures set forth in Example 1 were repeated. $0.5 \times 10^6$ HSC, $^{111}$In-labeled human CD34+ (hCD34+) peripheral blood stem cells were administered intravenously (i.v.) via an external jugular vein cannula to 2 month old, NOD-SCID, female mice (Non-obese diabetic/LtSz-scid/scid) obtained from the Jackson Laboratory, Bar Harbor, Me. The radiolabelled CD34+ stem cells were administered after pretreatment of the mouse with 11.0 mg of orosomucoid (0) i.v.

Mice were imaged and the biodistribution of the radiolabelled hCD34+ cells monitored as described above. Approximately 1 hour after infusion, the mice were sacrificed and the organs were harvested, and half of the organ was fixed in 10% neutral buffered formalin. Tissue sections were examined microscopically after immunohistochemical staining for human CD34 and in situ hybridization for the visualization of human DNA. Nuclear medicine monitoring for the first ten minutes and 1 hour post-infusion showed that the radiolabelled hCD34+ cells localized to the region of the liver/spleen.

Microscopic examination of the heart after immunohistologic staining for CD34 demonstrated hCD34+ cells in the endocardial blood vessel. A few hCD34+ cells could be seen in the lung in the alveolar septum. Clusters of cells with stem cell morphology could be seen in the hepatic sinusoid. In situ hybridization for human DNA clearly showed that hCD34+ cells were not found in the heart muscle or interventricular septum but were present in the lung.

Example 4

Asialoorosomucoid Followed by Orosomucoid Directs hCD34+ Cells to the Heart and Lung but not the Region of the Liver/Spleen Asialoorosomucoid (ASO)+Orosomucoid (O)/Low Dose HSC: When infused ASO caused HSC to localize in the heart, the protocol was changed to have the ASO bolus chased with a bolus of orosomucoid to test whether the accumulation in the heart would be maintained. HSC were again concentrated in the heart when an infusion of $0.5 \times 10^6$ HSC was preceded by 3.3 mg ASO, then 5.5 mg orosomucoid. This caused 44±5% of the infused cells to accumulate in the heart immediately after infusion. 37±3% of the infused cells remained in the heart region at 1 hr. The localization in the heart was the major concentrated signal from the cells, although the percent of infused was reduced from the ca. 75% seen in Example 1.

The preparation and procedures set forth in Example 1 were repeated. $0.5 \times 10^6$, In-labelled human CD34+ (hCD34+) peripheral blood stem cells were administered intravenously (i.v.) via an external jugular vein cannula to 2 month old, NOD-SCID, female mice (Non-obese diabetic/LtSz-scid/scid) obtained from the Jackson Laboratory, Bar Harbor, Me. The radiolabelled CD34+ stem cells were administered after pretreatment of the mouse with 3.3 mg of ASO i.v. followed by 5.5 mg 0 i.v.

Mice were imaged and the biodistribution of the radiolabelled hCD34+ cells monitored as described in Example 1. Nuclear medicine monitoring for the first ten minutes and 1 hour post-infusion showed that the radiolabelled hCD34+ cells localized to the heart.

Approximately 1 hour after infusion, the mouse was sacrificed and the organs were harvested and half the organ was fixed in 10% neutral buffered formalin.

Microscopic examination of the heart after immunohistologic staining for CD34 revealed clusters of hCD34+ cells in the interventricular septum, and cells within those clusters that were morphologically similar to the stained cells but that were CD34 negative. These images reflected the biodistribution depicted by nuclear medicine studies. The presence of hCD34+ cells in the heart was dramatically demonstrated by in situ hybridization. Both immunohistochemical staining for CD34 and in situ hybridization for human DNA demonstrated that the infused stem cells localized to the lung and could be readily seen in the alveolar septa, blood vessels, and other structures. Detection of human DNA revealed the presence of many more cells in the lung and heart than would have been predicted by CD34 staining. No hCD34+ cells or cells morphologically resembling hCD34+ cells were found in liver, spleen or kidney.

Example 5

HSC Administered in 5% Human Serum Albumin (without Orosomucoid or Asialoorosomucoid) Migrated Predominantly to the Lungs Plasma Albumin/High Dose HSC: When HSC were administered through the catheter without prior protein infusion, 78±13% of infused cells were found in the lungs at 0 hr. 54±10% at 1 hr, and 50±13% at 12 hr. Histological examination of lungs of mice similarly treated demonstrated infused cells within the alveolar septa and the vasculature.

$0.5 \times 10^6$, $^{111}$In-labeled HSC were administered intravenously (i.v.) via a cannula implanted in the external jugular vein of a two-month old, female NOD-SCID mouse in 0.1 ml saline containing 5% human serum albumin. Mice were imaged and the biodistribution of the radiolabelled hCD34+ cells monitored as described in Example 1.

Radiolabelled HSC, administered in saline containing 5% human serum albumin, migrated immediately to the lungs. Anatomic localization of the labelled cells was facilitated by the use of a $^{57}$Co-point source positioned at the level of the cannula exit site below the scapulae and nose. Moreover, the position marker at the cannula was verified to be at the diaphragm by CT whole body scans, transverse and coronal sections. The clip at the cannula exit site served as a landmark. The lungs were visualized below the nose marker and above the cannula marker and the liver and spleen below the cannula marker. Up to 95.4% of the injected dose was located in the lungs at initial imaging (Table 1, below). In four mice the values for the lungs ranged from 52.6-95.4% of whole body incorporation for the initial imaging time points. At 1 hour, HSC were located predominantly in the lungs with some counts visible in the blood circulation. In one mouse at 1 hour some localization was seen below the cannula marker, which may have been liver and spleen; however, the outline was indistinct. At 12 hour in that mouse, radiolabelled CD34+ stem cells were found in the liver/spleen region. However, more than 34.7% (range 34.7-68.5%) of the originally injected dose remained in the lungs of other animals imaged at 12 hour.

While the localization to the lungs immediately after injection (initial or 0 hour time points) varied from animal to animal, the percent of the original localization to the lungs remaining at subsequent scans was more constant. Using the dorsal images at 1 hour, 72.1-75.5% of the cells initially localized in the lung were retained in the lung region. Using the dorsal images at 12 hour, 78%, 72.1%, and 50.5% of the initial lung incorporation remained in the lungs of the three mice imaged.

Example 6

Orosomucoid Directs MSC to the Heart

Orosomucoid/Low Dose MSC: When a human mesenchymal stem cell infusion (0.56×10$^6$ cells) was preceded by 11 mg orosomucoid, 68±7% of infused cells were found in the heart at 0 hr, and 61±3% at 1 hr.

MSC were obtained from BioWhittaker, (Poietics Division, cryopreserved PT-2501>750000 cells per ampoule) and labelled with $^{111}$In as in previous examples, except that the MSC were labelled, washed, and injected in Basal Stem Cell Medium (Poietics) containing 5% human serum albumin (HSA). 0.56×10$^6$, $^{111}$In-labelled, human mesenchymal stem cells (MSC) were administered via an implanted DaVinci Microport Vascular System cannula in the external jugular vein of a two-month old, female NOD-SCID mouse in 0.21 ml of basal stem cell medium containing 5% human serum albumin (HSA). Immediately prior to administration of MSC, 11.0 mg of orosomucoid was administered i.v. in 0.2 ml.

Mice were imaged and the biodistribution of the radiolabelled MSCs cells monitored as described in Example 1. Gamma camera monitoring initially (0 hr) and at 1 hr post-infusion showed that the radiolabelled MSC localized to the region of the heart. Region of interest analysis of the images revealed that approximately 61.7-75.5% of the injected radioactivity initially localized to the heart and at 1 hr approximately 58-64% of the infused cells remained in this region. The positions of the cannula, diaphragm, heart, lungs, and liver were verified by CT scans (coronal sections). In situ hybridization showed human cells predominantly in the heart, but not the liver.

Example 7

Asialoorosomucoid Followed by Orosomucoid Directs MSC to the Liver/Spleen

MSC were obtained from BioWhittaker (Poietics Division, cryopreserved PT-2501>750000 cells per ampoule) and labelled with $^{111}$In. As in Example 6, the MSC were labelled, washed, and injected in Basal Stern Cell Medium (Poietics) containing 5% human serum albumin (HSA).

Asialoorosomucoid (ASO)+Orosomucoid/Low Dose MSC: This example was designed to compare the trafficking of MSC with HSC (Example 4) at the low cell dose, so the sequential infusion of ASO and orosomucoid used in Example 4 was applied. A human mesenchymal stem cell infusion (0.56×10$^6$ cells) was preceded by 4.3 mg ASO followed by 5.5 mg orosomucoid. 63±5% of the infused cells were found in the liver and spleen at 0 hr, and 57±7% at 1 hr.

0.56×10$^6$, $^{111}$In-labeled MSC were administered i.v. in 0.21 ml of basal stem cell medium containing 5% human serum albumin (HSA). Prior to administration of MSC, 0.1 ml containing 4.3 mg of ASO, followed by 0.1 ml containing 5.5 mg orosomucoid were administered i.v. The ASO, orosomucoid and MSC were administered via an implanted DaVinci Microport Vascular system cannula in the external jugular vein of a two-month old, female NOD-SCID mouse.

Mice were imaged and the biodistribution of the radiolabelled MSC monitored as in Example 1. Gamma camera monitoring initially and at 1 hr post-infusion showed that the radiolabelled MSC localized to the region of the liver/spleen. Region of interest analysis of the initial images revealed that approximately 59.2-66.7% of the injected radioactivity localized to the liver/spleen and at 1 hr approximately 51.9-61.1% of the infused cells remained in this region.

The positions of the cannula, diaphragm, heart, lungs, and liver were verified by CT scans. In situ hybridization confirmed the gamma camera biodistribution data. Cells containing human DNA were found predominantly in the liver.

Results. The results of the experiments described above are summarized in Table 1, below.

TABLE 1

| Stem Cells/ Protein Bolus | % Infused Cells in Lungs | % Infused Cells in Liver/Spleen | % Infused Cells In Heart |
|---|---|---|---|
| HSC/No Protein Bolus | 78 ± 3% at 0 hr 54 ± 10% at 12 hr | | |
| HSC/ Orosomucoid | | 74 ± 3% at 0 hr 74 ± 4% at 1.5 hr 63 ± 1% at 24 hr | |
| HSC/ASO | | | 77 ± 1% at 0 hr 75 ± 5% at 1.5 hr 52 ± 1% at 24 hr |
| MSC/No Protein Bolus | Saline only 95% at 0 hr 87% at 1 hr 61% at 24 hr 59% at 48 hr 5% Human serum 94% at 0 hr | | |

TABLE 1-continued

| Stem Cells/Protein Bolus | % Infused Cells in Liver/Spleen | % Infused Cells In Heart |
|---|---|---|
| | 87% at 1 hr | |
| | 59% at 24 hr | |
| | 57% at 48 hr | |
| | RPMI-1640 | |
| | 95% at 0 hr | |
| | 74% at 1 hr | |
| | 69% at 24 hr | |
| MSC/Orosomucoid | | 68 ± 7% at 0 hr |
| | | 61 ± 3% at 12 hr |
| MSC/ASO | 63 ± 5% at 0 hr | |
| | 57 ± 7% at 12 hr | |
| | % Infused Cells in Kidney | |
| MSC/No Protein Bolus | Saline only | |
| | 4% at 1 hr | |
| | 13% at 24 hr | |
| | 14% at 48 hr | |
| | 5% Human serum | |
| | 2% at 1 hr | |
| | 11% at 24 hr | |
| | 14% at 48 hr | |
| | RPMI-1640 | |
| | 7% at 1 hr | |
| | 9% at 24 hr | |

All publications, patents, patent applications, and other documents mentioned in the specification are indicative of the level of those skilled in the art to which this invention pertains. All publications, patents, patent applications, and other documents are herein incorporated by reference in their entirety for all purposes to the same extent as if each individual publication, patent, patent application, or other document was specifically and individually indicated to be incorporated herein by reference in its entirety for all purposes. Subheadings in the specification document are included solely for ease of review of the document and are not intended to be a limitation on the contents of the document in any way.

Although the foregoing invention has been described in some detail by way of illustration and example for purposes of clarity of understanding, it will be obvious that certain changes and modifications may be practiced within the scope of the appended claims.

What is claimed is:

1. A method for regenerating heart tissue in a mammalian subject which comprises administering to the subject a composition comprising asialoorosomucoid and a composition comprising asialodeterminant-bearing stem cells selected from the group consisting of CD34+ stem cells and hematopoietic stem cells, whereby heart tissue is regenerated.

2. The method of claim 1, wherein the asialodeterminant-bearing stem cell is a hematopoietic stem cell.

3. The method of claim 1, wherein the composition comprising asialoorosomucoid is administered before the composition comprising the asialodeterminant-bearing stem cells is administered.

4. The method of claim 1, wherein the composition comprising asialoorosomucoid is administered before and after the composition comprising the asialodeterminant-bearing stem cells is administered.

5. The method of claim 1, wherein the composition comprising asialoorosomucoid is administered during administration of the composition comprising the asialodeterminant-bearing stem cells.

6. The method of claim 1, wherein the mammalian subject is a human subject.

* * * * *